United States Patent
Olson et al.

(10) Patent No.: US 12,297,247 B2
(45) Date of Patent: May 13, 2025

(54) FUSION MOLECULES OF CTLA4 AND IL-15

(71) Applicant: NantCell, Inc., Culver City, CA (US)

(72) Inventors: Clifford Anders Olson, Long Beach, CA (US); Patrick Soon-Shiong, Los Angeles, CA (US); Shiho Tanaka, Redondo Beach, CA (US)

(73) Assignee: NantCell, Inc., Culver City, CA (US)

( * ) Notice: Subject to any disclaimer, the term of this patent is extended or adjusted under 35 U.S.C. 154(b) by 181 days.

(21) Appl. No.: 18/156,871

(22) Filed: Jan. 19, 2023

(65) Prior Publication Data

US 2023/0235003 A1 Jul. 27, 2023

Related U.S. Application Data

(60) Provisional application No. 63/302,044, filed on Jan. 22, 2022.

(51) Int. Cl.

| | | |
|---|---|---|
| C07K 14/54 | (2006.01) | |
| A61K 38/00 | (2006.01) | |
| A61K 39/00 | (2006.01) | |
| A61P 17/00 | (2006.01) | |
| A61P 35/00 | (2006.01) | |
| C07K 14/715 | (2006.01) | |
| C07K 16/28 | (2006.01) | |

(52) U.S. Cl.
CPC .......... *C07K 14/5443* (2013.01); *A61P 17/00* (2018.01); *A61P 35/00* (2018.01); *C07K 14/7155* (2013.01); *C07K 16/2818* (2013.01); *A61K 38/00* (2013.01); *A61K 2039/505* (2013.01); *C07K 2317/92* (2013.01); *C07K 2319/00* (2013.01)

(58) Field of Classification Search
CPC ............ C07K 14/5443; C07K 14/7155; C07K 2317/92; C07K 2319/00; C07K 19/00; C07K 2319/30; C07K 2319/32; C07K 2317/56; C07K 2317/565; C07K 2317/622; C07K 2317/73; C07K 2317/732; A61P 35/00; A61P 37/02; A61K 38/00; A61K 2039/505
See application file for complete search history.

(56) References Cited

FOREIGN PATENT DOCUMENTS

WO 2021250594 A1 12/2021

OTHER PUBLICATIONS

Sanseviero Emilio et al. (2019). Anti&8211;CTLA-4 Activates Intratumoral NK Cells and Combined with IL15/IL15R&945; Complexes Enhances Tumor Control. Cancer Immunology Research, 7(8):1371-1380.
Jochems Caroline et al. (2019). The multi-functionality of N-809, a novel fusion protein encompassing anti-PD-L1 and the IL-15 superagonist fusion complex. Oncoimmunolgy, 8(2):e1532764.
Tang Fei et al. (2018). Anti-CTLA-4 antibodies in cancer immunotherapy: selective depletion of intratumoral regulatory T cells or checkpoint blockade? Cell & Bioscience, 8(1):30.
O'Neill Rachel et al. (2019). Co-stimulatory and co-inhibitory pathways in cancer immunotherapy, Advances in Cancer Research. USAcademic Press, 145-194.
Wei X Q et al. (2001). The Sushi domain of soluble IL-15 receptor alpha is essential for binding IL-15 and inhibiting inflammatory and allogenic responses in vitro and in vivo. The Journal of Immunology, Williams & Wilkins Co, 167(1):277-282.
International Search Report from PCT Application No. PCT/US2023/060902 dated May 2, 2023.
Written Opinion from PCT Application No. PCT/US2023/060902 dated May 2, 2023.

*Primary Examiner* — Jeffrey Stucker
*Assistant Examiner* — Sarah Cooper Patterson
(74) *Attorney, Agent, or Firm* — Harness Dickey & Pierce P.L.C.

(57) ABSTRACT

Soluble fusion protein complexes, including domains from IL-15, IL-15 receptor, and αCTLA4 antibody for preventing, reducing the occurrence of, and/or treating cancer or an autoimmune disease or disorder in a subject are provided herein. The methods provided herein include administering to a subject a pharmaceutical composition of a soluble fusion protein complex.

12 Claims, 12 Drawing Sheets

Specification includes a Sequence Listing.

N-844-4  N-844-5

```
                    SEQUENCE LISTING

Sequence total quantity: 18
SEQ ID NO: 1            moltype = AA   length = 134
FEATURE                 Location/Qualifiers
REGION                  1..134
                        note = IL-15 N72D mutant with leader peptide
REGION                  1..20
                        note = MISC_FEATURE - Leader peptide
source                  1..134
                        mol_type = protein
                        organism = synthetic construct
SEQUENCE: 1
METDTLLLWV LLLWVPGSTG NWVNVISDLK KIEDLIQSMH IDATLYTESD VHPSCKVTAM   60
KCFLLELQVI SLESGDASIH DTVENLIILA NDSLSSNGNV TESGCKECEE LEEKNIKEFL  120
QSFVHIVQMF INTS                                                   134

SEQ ID NO: 2            moltype = DNA   length = 405
FEATURE                 Location/Qualifiers
misc_feature            1..405
                        note = IL15 N72D mutant with leader peptide
misc_feature            1..60
                        note = Leader peptide
source                  1..405
                        mol_type = other DNA
                        organism = synthetic construct
```

```
SEQUENCE: 2
atggagacag acacactcct gttatgggta ctgctgctct gggttccagg ttccaccggt    60
aactgggtga atgtaataag tgatttgaaa aaaattgaag atcttattca atctatgcat   120
attgatgcta ctttatatac ggaaagtgat gttcacccca gttgcaaagt aacagcaatg   180
aagtgctttc tcttggagtt acaagttatt tcacttgagt ccggagatgc aagtattcat   240
gatacagtag aaaatctgat catcctagca aacgacagtt tgtcttctaa tgggaatgta   300
acagaatctg gatgcaaaga atgtgaggaa ctggaggaaa aaatattaa agaatttttg    360
cagagtttta tacatattgt ccaaatgttc atcaacactt cttaa                   405

SEQ ID NO: 3              moltype = AA  length = 214
FEATURE                   Location/Qualifiers
REGION                    1..214
                          note = Anti-CTLA4 light chain
BINDING                   27..34
                          note = CDR1
BINDING                   46..56
                          note = CDR2
BINDING                   89..96
                          note = CDR3
source                    1..214
                          mol_type = protein
                          organism = synthetic construct
SEQUENCE: 3
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ GDAWPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 4              moltype = AA  length = 534
FEATURE                   Location/Qualifiers
REGION                    1..534
                          note = N-terminal sushi domain fusion with anti-CTLA4 heavy
                             chain
source                    1..534
                          mol_type = protein
                          organism = synthetic construct
SEQUENCE: 4
ITCPPPMSVE HADIWVKSYS LYSRERYICN SGFKRKAGTS SLTECVLNKA TNVAHWTTPS    60
LKCIRGGGGS GGGGSGGGGS EVQLVESGGG LVQPGGSLRL SCAASGFTFT SYSMHWVRQA   120
PGKGLEWVSG ISGSGRSTSY ADSVKGRFTI SRDNSKNTLY LQMNSLRAED TAVYYCARDL   180
MAFNLVRAGG FDVWGQGTLV TVSSASTKGP SVFPLAPSSK STSGGTAALG CLVKDYFPEP   240
VTVSWNSGAL TSGVHTFPAV LQSSGLYSLS SVVTVPSSSL GTQTYICNVN HKPSNTKVDK   300
KVEPKSCDKT HTCPPCPAPE LLGGPSVFLF PPKPKDTLMI SRTPEVTCVV VDVSHEDPEV   360
KFNWYVDGVE VHNAKTKPRE EQYNSTYRVV SVLTVLHQDW LNGKEYKCKV SNKALPAPIE   420
KTISKAKGQP REPQVYTLPP SRDELTKNQV SLTCLVKGFY PSDIAVEWES NGQPENNYKT   480
TPPVLDSDGS FFLYSKLTVD KSRWQQGNVF SCSVMHEALH NHYTQKSLSL SPGK         534

SEQ ID NO: 5              moltype = AA  length = 534
FEATURE                   Location/Qualifiers
REGION                    1..534
                          note = C-terminal sushi domain fusion with anti-CTLA4 heavy
                             chain
source                    1..534
                          mol_type = protein
                          organism = synthetic construct
SEQUENCE: 5
EVQLVESGGG LVQPGGSLRL SCAASGFTFT SYSMHWVRQA PGKGLEWVSG ISGSGRSTSY    60
ADSVKGRFTI SRDNSKNTLY LQMNSLRAED TAVYYCARDL MAFNLVRAGG FDVWGQGTLV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK KVEPKSCDKT HTCPPCPAPE   240
LLGGPSVFLF PPKPKDTLMI SRTPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVYTLPP   360
SRDELTKNQV SLTCLVKGFY PSDIAVEWES NGQPENNYKT TPPVLDSDGS FFLYSKLTVD   420
KSRWQQGNVF SCSVMHEALH NHYTQKSLSL SPGKGGGGSG GGGSGGGGSI TCPPPMSVEH   480
ADIWVKSYSL YSRERYICNS GFKRKAGTSS LTECVLNKAT NVAHWTTPSL KCIR         534

SEQ ID NO: 6              moltype = AA  length = 543
FEATURE                   Location/Qualifiers
REGION                    1..543
                          note = Anti-CTLA4 scFv-sushi-Fc
source                    1..543
                          mol_type = protein
                          organism = synthetic construct
SEQUENCE: 6
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ GDAWPWTFGQ GTKVEIKGGG GSGGGGSGGG   120
GSEVQLVESG GGLVQPGGSL RLSCAASGFT FTSYSMHWVR QAPGKGLEWV SGISGSGRST   180
SYADSVKGRF TISRDNSKNT LYLQMNSLRA EDTAVYYCAR DLMAFNLVRA GGFDVWGQGT   240
LVTVSSITCP PPMSVEHADI WVKSYSLYSR ERYICNSGFK RKAGTSSLTE CVLNKATNVA   300
```

```
HWTTPSLKCI REPKSSDKTH TCPPCPAPEL LGGGPSVFLFP PKPKDTLMIS RTPEVTCVVV   360
DVSHEDPEVK FNWYVDGVEV HNAKTKPREE QYNSTYRVVS VLTVLHQDWL NGKEYKCKVS   420
NKALPAPIEK TISKAKGQPR EPQVYTLPPS RDELTKNQVS LTCLVKGFYP SDIAVEWESN   480
GQPENNYKTT PPVLDSDGSF FLYSKLTVDK SRWQQGNVFS CSVMHEALHN HYTQKSLSLS   540
PGK                                                                543

SEQ ID NO: 7           moltype = AA  length = 375
FEATURE                Location/Qualifiers
REGION                 1..375
                       note = Anti-CTLA4 scFv-IL-15 (N72D)
source                 1..375
                       mol_type = protein
                       organism = synthetic construct
SEQUENCE: 7
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ GDAWPWTFGQ GTKVEIKGGG GSGGGGSGGG   120
GSEVQLVESG GGLVQPGGSL RLSCAASGFT FTSYSMHWVR QAPGKGLEWV SGISGSGRST   180
SYADSVKGRF TISRDNSKNT LYLQMNSLRA EDTAVYYCAR DLMAFNLVRA GGFDVWGQGT   240
LVTVSSGGGG SGGGGSGGGG SNWVNVISDL KKIEDLIQSM HIDATLYTES DVHPSCKVTA   300
MKCFLLELQV ISLESGDASI HDTVENLIIL ANDSLSSNGN VTESGCKECE ELEEKNIKEF   360
LQSFVHIVQM FINTS                                                    375

SEQ ID NO: 8           moltype = AA  length = 297
FEATURE                Location/Qualifiers
REGION                 1..297
                       note = Sushi-Fc fusion
source                 1..297
                       mol_type = protein
                       organism = synthetic construct
SEQUENCE: 8
ITCPPPMSVE HADIWVKSYS LYSRERYICN SGFKRKAGTS SLTECVLNKA TNVAHWTTPS    60
LKCIREPKSS DKTHTCPPCP APELLGGPSV FLFPPKPKDT LMISRTPEVT CVVVDVSHED   120
PEVKFNWYVD GVEVHNAKTK PREEQYNSTY RVVSVLTVLH QDWLNGKEYK CKVSNKALPA   180
PIEKTISKAK GQPREPQVYT LPPSRDELTK NQVSLTCLVK GFYPSDIAVE WESNGQPENN   240
YKTTPPVLDS DGSFFLYSKL TVDKSRWQQG NVFSCSVMHE ALHNHYTQKS LSLSPGK      297

SEQ ID NO: 9           moltype = AA  length = 558
FEATURE                Location/Qualifiers
REGION                 1..558
                       note = Sushi-Fc-anti-CTLA4 scFv fusion
source                 1..558
                       mol_type = protein
                       organism = synthetic construct
SEQUENCE: 9
ITCPPPMSVE HADIWVKSYS LYSRERYICN SGFKRKAGTS SLTECVLNKA TNVAHWTTPS    60
LKCIREPKSS DKTHTCPPCP APELLGGPSV FLFPPKPKDT LMISRTPEVT CVVVDVSHED   120
PEVKFNWYVD GVEVHNAKTK PREEQYNSTY RVVSVLTVLH QDWLNGKEYK CKVSNKALPA   180
PIEKTISKAK GQPREPQVYT LPPSRDELTK NQVSLTCLVK GFYPSDIAVE WESNGQPENN   240
YKTTPPVLDS DGSFFLYSKL TVDKSRWQQG NVFSCSVMHE ALHNHYTQKS LSLSPGKGGG   300
GSGGGGSGGG GSDIQMTQSP SSLSASVGDR VTITCQASQD ISNYLNWYQQ KPGKAPKLLI   360
YDASNLETGV PSRFSGSGSG TDFTFTISSL QPEDIATYYC QQGDAWPWTF GQGTKVEIKG   420
GGGSGGGGSG GGGSEVQLVE SGGGLVQPGG SLRLSCAASG FTFTSYSMHW VRQAPGKGLE   480
WVSGISGSGR STSYADSVKG RFTISRDNSK NTLYLQMNSL RAEDTAVYYC ARDLMAFNLV   540
RAGGFDVWGQ GTLVTVSS                                                 558

SEQ ID NO: 10          moltype = AA  length = 454
FEATURE                Location/Qualifiers
REGION                 1..454
                       note = Anti-CTLA4 heavy chain
BINDING                27..35
                       note = CDR1
BINDING                47..61
                       note = CDR2
BINDING                97..113
                       note = CDR3
source                 1..454
                       mol_type = protein
                       organism = synthetic construct
SEQUENCE: 10
EVQLVESGGG LVQPGGSLRL SCAASGFTFT SYSMHWVRQA PGKGLEWVSG ISGSGRSTSY    60
ADSVKGRFTI SRDNSKNTLY LQMNSLRAED TAVYYCARDL MAFNLVRAGG FDVWGQGTLV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK KVEPKSCDKT HTCPPCPAPE   240
LLGGPSVFLF PPKPKDTLMI SRTPEVTCVV VDVSHEDPEV KFNWYVDGVE VHNAKTKPRE   300
EQYNSTYRVV SVLTVLHQDW LNGKEYKCKV SNKALPAPIE KTISKAKGQP REPQVYTLPP   360
SRDELTKNQV SLTCLVKGFY PSDIAVEWES NGQPENNYKT TPPVLDSDGS FFLYSKLTVD   420
KSRWQQGNVF SCSVMHEALH NHYTQKSLSL SPGK                               454

SEQ ID NO: 11          moltype = AA  length = 6
```

```
FEATURE                 Location/Qualifiers
REGION                  1..6
                        note = Heavy chain CDR1
source                  1..6
                        mol_type = protein
                        organism = synthetic construct
SEQUENCE: 11
TSYSMH                                                                        6

SEQ ID NO: 12           moltype = AA  length = 10
FEATURE                 Location/Qualifiers
REGION                  1..10
                        note = Heavy chain CDR2
source                  1..10
                        mol_type = protein
                        organism = synthetic construct
SEQUENCE: 12
GISGSGRSTS                                                                   10

SEQ ID NO: 13           moltype = AA  length = 16
FEATURE                 Location/Qualifiers
REGION                  1..16
                        note = Heavy chain CDR3
source                  1..16
                        mol_type = protein
                        organism = synthetic construct
SEQUENCE: 13
RDLMAFNLVR AGGFDV                                                            16

SEQ ID NO: 14           moltype = AA  length = 10
FEATURE                 Location/Qualifiers
REGION                  1..10
                        note = Light chain CDR1
source                  1..10
                        mol_type = protein
                        organism = synthetic construct
SEQUENCE: 14
QASQDISNYL                                                                   10

SEQ ID NO: 15           moltype = AA  length = 7
FEATURE                 Location/Qualifiers
REGION                  1..7
                        note = Light chain CDR2
source                  1..7
                        mol_type = protein
                        organism = synthetic construct
SEQUENCE: 15
DASNLET                                                                       7

SEQ ID NO: 16           moltype = AA  length = 8
FEATURE                 Location/Qualifiers
REGION                  1..8
                        note = Light chain CDR3
source                  1..8
                        mol_type = protein
                        organism = synthetic construct
SEQUENCE: 16
QGDAWPWT                                                                      8

SEQ ID NO: 17           moltype = AA  length = 114
FEATURE                 Location/Qualifiers
REGION                  1..114
                        note = IL-15 N72D mutant without leader peptide
source                  1..114
                        mol_type = protein
                        organism = synthetic construct
SEQUENCE: 17
NWVNVISDLK KIEDLIQSMH IDATLYTESD VHPSCKVTAM KCFLLELQVI SLESGDASIH            60
DTVENLIILA NDSLSSNGNV TESGCKECEE LEEKNIKEFL QSFVHIVQMF INTS                 114

SEQ ID NO: 18           moltype = DNA  length = 345
FEATURE                 Location/Qualifiers
source                  1..345
                        mol_type = other DNA
                        organism = synthetic construct
SEQUENCE: 18
aactgggtga atgtaataag tgatttgaaa aaattgaag atcttattca atctatgcat             60
attgatgcta ctttatatac ggaaagtgat gttcacccca gttgcaaagt aacagcaatg          120
aagtgctttc tcttggagtt acaagttatt tcacttgagt ccggagatgc aagtattcat          180
```

```
gatacagtag aaaatctgat catcctagca aacgacagtt tgtcttctaa tgggaatgta    240
acagaatctg gatgcaaaga atgtgaggaa ctggaggaaa aaaatattaa agaatttttg    300
cagagttttg tacatattgt ccaaatgttc atcaacactt cttaa                   345
```

FUSION MOLECULES OF CTLA4 AND IL-15

CROSS-REFERENCE TO RELATED APPLICATIONS

This patent application claims the benefit under 35 U.S.C. § 119(e) to U.S. Provisional Application No. 63/302,044 filed on 22 Jan. 2022. The entire contents of U.S. 63/302,044 are hereby incorporated by reference.

Statement of a Sequence Listing

The present disclosure contains references to amino acid sequences and nucleic acid sequences which have been submitted concurrently herewith as a sequence listing ST.26 XML file entitled "000112us_SequenceListing.XML," file size 29.8 KiloBytes (KB), created on 10 Jan. 2023. The aforementioned sequence listing is hereby incorporated by reference in its entirety pursuant to 37 C.F.R. § 1.52(e)(5).

FIELD

The present disclosure relates to multimeric soluble fusion protein complexes and their uses in treating disease, such as cancer and autoimmune diseases.

BACKGROUND

Cytotoxic T lymphocyte antigen 4 (CTLA4), a member of the immunoglobulin superfamily, is a molecule expressed by activated T cells. CTLA4 is similar to the T-cell co-stimulatory molecule CD28, and both molecules bind to B7-1 (CD80) and B7-2 (CD86) on antigen-presenting cells (APCs). However, CTLA4 transmits an inhibitory signal to T cells, whereas CD28 transmits a stimulatory signal.

Interleukin-15 (IL-15) can promote both innate and adaptive immune reactions by stimulating CD8$^+$/CD4$^+$ T cells and natural killer cells (NK) while showing no effect in activating T-regulatory (T$_{reg}$) cells or inducing activation-associated death among effector T cells and NK cells. Thus, IL-15 is a promising molecule for antitumor immune therapy. Bessard & al. (2009) *Mol Cancer Ther.* 8(9):2736-45.

Although IL-15 has a great potential for therapeutic use, the primary limitations in clinical development of recombinant human IL-15 (rhIL-15) are low production yields in standard mammalian cell expression systems and a short serum half-life. Ward & al. (2009) *Protein Expr Purif.* 68(1):42-48.

SUMMARY

Disclosed herein are soluble fusion protein complexes comprising a first domain, which comprises an IL-15 peptide or variant thereof, a second domain comprising a fusion polypeptide comprising an IL-15Rα Sushi peptide (IL15RαSu) and an αCTLA4 antibody heavy chain, and a third domain comprising an αCTLA4 antibody light chain. The IL-15 peptide or variant binds to the IL15RαSu peptide to form a soluble fusion protein complex. The soluble fusion protein complex and pharmaceutical compositions thereof modulate immune responses. Also disclosed herein are methods to prevent or treat cancer wherein an immune response is enhanced, and methods to prevent or treat autoimmune diseases or disorders wherein an immune response is decreased.

In some embodiments, the soluble fusion protein complex comprises: (a) a first domain having an IL-15 peptide having sequence identity (e.g., at least about 85% sequence identity) to SEQ ID NO: 17; (b) a second domain having a fusion polypeptide comprising an IL15RαSu peptide and an αCTLA4 antibody heavy chain having sequence identity (e.g., at least about 85% sequence identity) to SEQ ID NO: 10; and (c) a third domain having an αCTLA4 antibody light chain having sequence identity (e.g., at least about 85% sequence identity) to SEQ ID NO: 3. In some embodiments, the IL15RαSu peptide has a sequence identity (e.g., at least about 85% sequence identity) to SEQ ID NO: 8. The first domain may comprise an IL-15 variant comprising an N72D mutation (IL-15N72D). Further, the IL-15 peptide in the first domain may comprise or lack a leader sequence.

In some embodiments, the soluble fusion protein complex may include complementarity determining regions on the αCTLA4 antibody heavy chain (e.g., one or more of SEQ ID NOs: 11-13) of the second domain and/or on the αCTLA4 antibody light chain (e.g., one or more of SEQ ID NOs: 14-16) of the third domain. The fusion polypeptide of the second domain may further include a linker between the IL15RαSu peptide and the αCTLA4 antibody heavy chain. The fusion polypeptide may have a sequence identity (e.g., at least about 85% sequence identity) to SEQ ID NO: 4 or SEQ ID NO: 5.

In further embodiments, the soluble fusion protein complex may be formulated in a pharmaceutical composition further comprising a pharmaceutically acceptable carrier. The pharmaceutical composition may be formatted for various routes of administration, including for parenteral injection. The pharmaceutical composition may be formulated for subcutaneous, intravenous, intramuscular, intravesicular, intratumoral, or intraperitoneal injection.

Also described is a method of preventing or treating cancer comprising administering to a subject in need thereof a soluble fusion protein complex as described herein comprising a first domain having an IL-15 peptide or variant thereof, a second domain having a fusion polypeptide comprising an IL15RαSu peptide and an αCTLA4 antibody heavy chain, and a third domain having an αCTLA4 antibody light chain. The soluble fusion protein complex may be formulated in a pharmaceutical composition appropriate for administration to the subject to prevent or treat the cancer.

Also described is a method of preventing or treating an autoimmune disease or disorder comprising administering to a subject in need thereof a soluble fusion protein complex as described herein comprising a first domain having an IL-15 peptide or variant thereof, a second domain having a fusion polypeptide comprising an IL15RαSu peptide and an αCTLA4 antibody heavy chain, and a third domain having an αCTLA4 antibody light chain. The soluble fusion protein complex may be formulated in a pharmaceutical composition appropriate for administration to the subject to prevent or treat the autoimmune disease or disorder.

Various objects, features, aspects, and advantages will become more apparent from the following detailed description of preferred embodiments, along with the accompanying drawings.

BRIEF DESCRIPTION OF THE DRAWINGS

FIG. 1 depicts a key by which

FIG. 2 depicts the three "TxM" configurations. Configuration A (TxM-A also referred to as N-844-1) has the antibody domain conjugated to the IL15RαSu peptide. Configuration B (TxM-B also referred to as N-844-2) has the antibody domain conjugated to the IL-15 peptide. Configuration C (TxM-C also referred to as N-844-3) has the antibody domain conjugated to the $C_H3$ half of the Fc domain.

FIG. 3 depicts two CTLA4-targeted IL-15 molecules that are not assembled in "TxM" configuration. As used herein, "IL-15/αCTLA-4" also refers to N-844-4 and "αCTLA-4/IL-15" also refers to N-844-5.

FIG. 6A shows the tumor grown in individual mice treated with αOX40 antibodies+αCTLA4-7. FIG. 6B shows the tumor grown in individual mice treated with αOX40 antibodies+ α-CTLA4-TxM-A (N-844-2). FIG. 6C shows the tumor grown in individual mice treated with αOX40 antibodies+ IL-15-α-CTLA4 (N-844-4). FIG. tumor grown in individual FIG. 6E shows the mice treated with αOX40 antibodies+ αCTLA4-7+NAI (N-803).

FIGS. 7A and 7B show the efficacy of treatment in injected and distal tumors, respectively. FIG. 7C shows the tolerability of treatments through Day 18.

DETAILED DESCRIPTION

Figure 1:
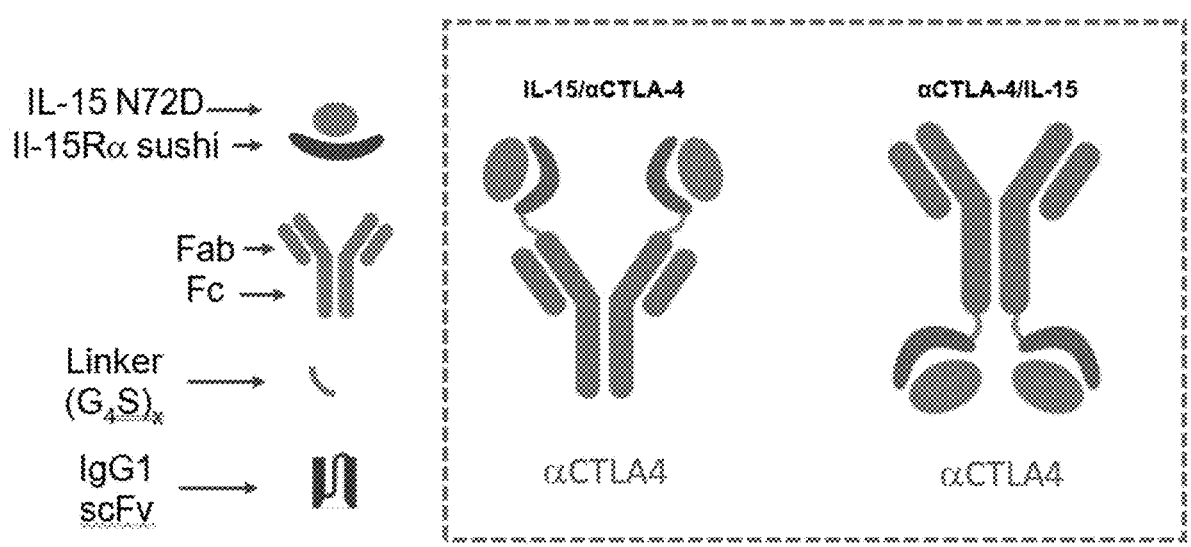

Definitions. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used. It is also to be understood that the terminology used herein is for the purpose of describing particular embodiments only and is not intended to be limiting.

The articles "a" and "an" are used herein to refer to one or to more than one (i.e., to at least one) of the grammatical object of the article. By way of example, "an element" means one element or more than one element. Thus, recitation of "a cell," for example, includes a plurality of the cells of the same type. Furthermore, to the extent that the terms "including," "includes," "having," "has," "with," or variants thereof are used in either the detailed description and/or the claims, such terms are intended to be inclusive in a manner similar to the term "comprising."

As used in this specification and the appended claims, "or" is generally employed in its sense including "and/or" unless the content clearly dictates otherwise.

"About" as used herein when referring to a measurable value such as an amount, a temporal duration, and the like, is meant to encompass variations that would round out from a value past the last significant digit. For example, the designation "about 2.5" reads a range of values from 2.45 (which would round up to 2.5) to 2.54 (which would round down to 2.5).

The term "ameliorate" is meant decrease, suppress, attenuate, diminish, arrest, or stabilize the development or progression of a disease.

"Antibody" or "immunoglobulin" encompasses both polyclonal and monoclonal antibodies. The preferred antibody is a monoclonal antibody reactive with the antigen. The term "antibody" also encompasses mixtures of more than one antibody reactive with the antigen (e.g., a cocktail of different types of monoclonal antibodies reactive with the antigen). Furthermore, "antibody" encompasses whole antibodies, biologically functional fragments thereof, single-chain antibodies, and genetically altered antibodies such as chimeric antibodies comprising portions from more than one species, bifunctional antibodies, antibody conjugates, humanized antibodies, and fully human antibodies. Biologically functional antibody fragments, which can also be used, are those peptide fragments derived from an antibody that are sufficient for binding to the antigen. "Antibody" as used herein is also meant to include the entire antibody as well as any antibody fragments (e.g. F(ab')2, Fab', Fab, Fv) capable of binding the epitope, antigen or antigenic fragment of interest. By "binding to" a molecule is meant having a physicochemical affinity for that molecule.

The term "cancer" as used herein is meant a disease characterized by unregulated cell growth or replication as is known in the art. "Cancer" includes colorectal cancer, as well as, for example, leukemia, e.g., acute myelogenous leukemia (AML), chronic myelogenous leukemia (CML), acute lymphocytic leukemia (ALL), and chronic lymphocytic leukemia, AIDS related cancers such as Kaposi's sarcoma; breast cancers; bone cancers such as Osteosarcoma, Chondrosarcomas, Ewing's sarcoma, Fibrosarcomas, Giant cell tumors, Adamantinomas, and Chordomas; Brain cancers such as Meningiomas, Glioblastomas, Lower-Grade Astrocytomas, Oligodendrocytomas, Pituitary Tumors, Schwannomas, and Metastatic brain cancers; cancers of the head and neck including various lymphomas such as mantle cell lymphoma, non-Hodgkin's lymphoma, adenoma, squamous cell carcinoma, laryngeal carcinoma, gallbladder and bile duct cancers, cancers of the retina such as retinoblastoma, cancers of the esophagus, gastric cancers, multiple myeloma, ovarian cancer, uterine cancer, thyroid cancer, testicular cancer, endometrial cancer, melanoma, lung cancer, bladder cancer, prostate cancer, lung cancer (including non-small cell lung carcinoma), pancreatic cancer, sarcomas, Wilms' tumor, cervical cancer, skin cancers, nasopharyngeal carcinoma, liposarcoma, epithelial carcinoma, renal cell carcinoma, gallbladder adenocarcinoma, parotid adenocarcinoma, endometrial sarcoma, multidrug resistant cancers; and proliferative diseases, such as neovascularization associated with tumor angiogenesis, macular degeneration (e.g., wet/dry AMD), corneal neovascularization, diabetic retinopathy, neovascular glaucoma, myopic degeneration and other proliferative diseases and conditions such as restenosis and polycystic kidney disease, and other cancer or proliferative disease that can respond to the modulation of its environment, alone or in combination with other therapies.

The term "disease" is meant any condition or disorder that damages or interferes with the normal function of a cell, tissue, or organ. Examples of diseases that can be treated with the compositions disclosed herein include neoplasia, autoimmune diseases, viral infections, and senescent cell- and age-related diseases.

"Effective amount" and "therapeutically effective amount" of a formulation or formulation component convey a sufficient amount of the formulation or component, alone or in a combination, to provide the desired effect. For example, "an effective amount" is an amount of a soluble fusion protein complex, alone or in a combination, required to ameliorate the symptoms of a disease relative to an untreated patient. The effective amount of the soluble fusion protein complex used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

A "high affinity" natural killer (haNK) cell is an NK cell engineered to incorporate a high binding affinity receptor i.e. a CD16 allele that binds to an administered antibody. A T-haNK is a haNK natural killer cell additionally engineered to include an antigen-targeting, scFv.

"Identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window. The degree of amino acid or nucleic acid sequence identity for purposes of the present disclosure is determined using the BLAST algorithm, described in Altschul & al. (199) $J.$ $Mol.$ $Biol.$ 215:403-10, which is incorporated herein by reference. The BLAST algorithm is publicly available through software provided by the National Center for Biotechnology Infor- mation (at the web address www.ncbi.nlm.nih.gov). This algorithm identifies high scoring sequence pairs (HSPS) by identifying short words of length W in the query sequence, which either match or satisfy some positive-valued threshold score T when aligned with a word of the same length in a database sequence. T is referred to as the neighborhood word score threshold (Altschul & al., supra.). Initial neighborhood word hits act as seeds for initiating searches to find longer HSPs containing them. The word hits are then extended in both directions along each sequence for as far as the cumu- lative alignment score can be increased. Cumulative scores are calculated for nucleotides sequences using the param- eters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maxi- mum achieved value; the cumulative score goes to zero or below due to the accumulation of one or more negative- scoring residue alignments; or the end of either sequence is reached. For determining the percent identity of an amino acid sequence or nucleic acid sequence, the default param- eters of the BLAST programs can be used. For analysis of amino acid sequences, the BLASTP defaults are: word length (W), 3; expectation (E), 10; and the BLOSUM62 scoring matrix. For analysis of nucleic acid sequences, the BLASTN program defaults are word length (W), 11; expec- tation (E), 10; M=5; N=−4; and a comparison of both strands. The TBLASTN program (using a protein sequence to query nucleotide sequence databases) uses as defaults a word length (W) of 3, an expectation (E) of 10, and a BLOSUM 62 scoring matrix (see Henikoff & Henikoff (1989) $Proc.$ $Natl.$ $Acad.$ $Sci.$ $USA$ 89:10915, which is incorporated herein by reference).

In addition to calculating percent sequence identity, the BLAST algorithm also performs a statistical analysis of the similarity between two sequences (see, e.g., Karlin & Alt- schul (1993) $Proc.$ $Nat'l.$ $Acad.$ $Sci.$ $USA$ 90:5873-87, which is incorporated herein by reference). The smallest sum probability (P(N)), provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01.

The term "immune effector cell," as used herein, refers to a cell that is involved in an immune response, e.g., in the promotion of an immune effector response. Examples of immune effector cells include T cells, e.g., alpha/beta ($\alpha/\beta$) T cells and gamma/delta ($\gamma/\delta$) T cells, B cells, natural killer (NK) cells, natural killer T (NK-T) cells, mast cells, and myeloid-derived phagocytes. "Immune effector function or immune effector response," as that term is used herein, refers to function or response, e.g., of an immune effector cell, that enhances or promotes an immune attack of a target cell. For example, an immune effector function or response refers a property of a T or NK cell that promotes killing or the inhibition of growth or proliferation, of a target cell. In the case of a T cell, primary stimulation and co-stimulation are examples of immune effector function or response.

As used herein, the term "in combination" in the context of the administration of a therapy to a subject refers to the use of more than one therapy for therapeutic benefit. The term "in combination" in the context of the administration can also refer to the prophylactic use of a therapy to a subject when used with at least one additional therapy. The use of the term "in combination" does not restrict the order in which the therapies (e.g., a first and second therapy) are administered to a subject. A therapy can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 min- ute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the adminis- tration of a second therapy to a subject which had, has, or is susceptible to cancer. The therapies are administered to a subject in a sequence and within a time interval such that the therapies can act together. In a particular embodiment, the therapies are administered to a subject in a sequence and within a time interval such that they provide an increased benefit than if they were administered otherwise. Any addi- tional therapy can be administered in any order with the other additional therapy.

"Parenteral" administration of an immunogenic compo- sition includes, e.g., subcutaneous (s.c.), intravenous (i.v.), intramuscular (i.m.), or intrasternal injection, or infusion techniques.

"Patient" or "individual" or "subject" are used inter- changeably herein, and refers to a mammalian subject to be treated, interchangeably refer to a mammal, preferably a human or anon-human primate, but also domesticated mam- mals (e.g., canine or feline), laboratory mammals (e.g., mouse, rat, rabbit, hamster, guinea pig), and agricultural mammals (e.g., equine, bovine, porcine, ovine). In certain embodiments, the subject can be human (e.g., adult male, adult female, adolescent male, adolescent female, male child, female child) under the care of a physician or other health worker. In certain embodiments the subject may not be under the care of a physician or other health worker.

A "pharmaceutically acceptable" component/carrier etc. is one that is suitable for use with humans and/or animals without undue adverse side effects (such as toxicity, irritation, and allergic response) commensurate with a reasonable benefit/risk ratio.

"Prevent," "preventing," and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

"Reduces" means a negative alteration of a condition, disorder, or disease compared to a "healthy" or "appropriate" control subject that does not have the condition, disorder, or disease. The negative alteration may be of at least about 5%, at least about 10%, at least about 25%, at least about 50%, at least about 75%, or at least about 100%.

"Specifically binds" means that a molecule, protein, peptide, antibody, or antibody fragment recognizes and binds a polypeptide of the invention, but which does not substantially recognize and bind other molecules in a sample, for example, a biological sample, which may include a polypeptide of the invention.

"Treat," "treating," and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. Treatment may include administration of a fusion molecule of CTLA4 and IL-15 or an analog thereof. It will be appreciated that, although not precluded, treating a disorder or condition does not require that the disorder, condition, or symptoms associated therewith be completely eliminated.

Treatment of patients with neoplasia may include any of the following: Adjuvant therapy (also called adjunct therapy or adjunctive therapy) to destroy residual tumor cells that may be present after the known tumor is removed by the initial therapy (e.g. surgery), thereby preventing possible cancer reoccurrence; neoadjuvant therapy given prior to the surgical procedure to shrink the cancer; induction therapy to cause a remission, typically for acute leukemia; consolidation therapy (also called intensification therapy) given once a remission is achieved to sustain the remission; maintenance therapy given in lower or less frequent doses to assist in prolonging a remission; first line therapy (also called standard therapy); second (o$^r$ 3rd, 4th, etc.) line therapy (also called salvage therapy) is given if a disease has not responded or reoccurred after first line therapy; and palliative therapy (also called supportive therapy) to address symptom management without expecting to significantly reduce the cancer.

"Tumor" means a mass of transformed cells that are characterized by neoplastic uncontrolled cell multiplication and at least in part, by containing angiogenic vasculature. The abnormal neoplastic cell growth is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e. a metastatic tumor), a tumor also can be nonmalignant (i.e. non-metastatic tumor). Tumors are hallmarks of cancer, a neoplastic disease the natural course of which is fatal.

Certain methodologies of the instant invention include a step that involves comparing a value, level, feature, characteristic, property, etc. to a "suitable control," referred to interchangeably herein as an "appropriate control". A "suitable control" or "appropriate control" is a control or standard familiar to one of ordinary skill in the art useful for comparison purposes. In one embodiment, a "suitable control" or "appropriate control" is a value, level, feature, characteristic, property, etc. determined prior to performing a treatment and/or agent administration methodology, as described herein. For example, a transcription rate, mRNA level, translation rate, protein level, biological activity, cellular characteristic or property, genotype, phenotype, etc. can be determined prior to introducing a treatment and/or agent of the invention to a subject. In another embodiment, a "suitable control" or "appropriate control" is a value, level, feature, characteristic, property, etc. determined in a cell or organism, e.g., a control or normal cell or organism, exhibiting, for example, normal or healthy (e.g., non-diseased) traits. In yet another embodiment, a "suitable control" or "appropriate control" is a predefined value, level, feature, characteristic, property, etc.

Genes: All genes, gene names, and gene products disclosed herein are intended to correspond to homologs from any species for which the compositions and methods disclosed herein are applicable. It is understood that when a gene or gene product from a particular species is disclosed, this disclosure is intended to be exemplary only, and is not to be interpreted as a limitation unless the context in which it appears clearly indicates. Thus, for example, for the genes or gene products disclosed herein, are intended to encompass homologous and/or orthologous genes and gene products from other species.

GenBank and NCBI submissions indicated by accession number cited herein are incorporated herein by reference.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Any compositions or methods provided herein can be combined with one or more of any of the other compositions and methods provided herein.

Interleukin-15. Human IL-15 (huIL-15) is a member of the small four α-helix bundle family of cytokines that associates with the huIL-15 receptor α-chain (huIL-15Rα) with a high binding affinity (equilibrium dissociation constant $(K_D)$~$10^{-11}$ M). The resulting complex trans-presents to the human IL-2/15 receptor β/common γ chain (huIL-15βγC) complexes displayed on T cell & NK surfaces. This cytokine/receptor interaction results in expansion and activation of effector T cells and NK cells, which play an important role in eradicating virally infected and malignant cells. Normally, huIL-15 and huIL-15Rα are co-produced in dendritic cells to form complexes intracellularly that are subsequently secreted and displayed as heterodimeric molecules on cell surfaces. Thus, the characteristics of huIL-15 and huIL-15Rα interactions suggest that these inter chain binding domains could serve as a human-derived immunostimulatory scaffold to make soluble dimeric molecules capable of target-specific binding.

In certain aspects of the soluble fusion protein complexes of the invention, the IL-15 peptide may be an IL-15 variant having a different amino acid sequence than native IL-15 peptide. The huIL-15 and variants thereof are referred to using the native amino acid, its position in the mature sequence and the variant amino acid. For example, huIL15N72D refers to human IL-15 comprising a substitution of N to D at position 72. In one aspect, the IL-15 variant functions as an IL-15 agonist as demonstrated, e.g., by increased binding activity for the IL-15RβγC receptors compared to the native IL-15 peptide. Alternatively, the IL-15 variant functions as an IL-15 antagonist as demonstrated by e.g., decreased binding activity for the IL-15RβγC receptors compared to the native IL-15 sequence.

IL-15:IL-15Rα complex. The formation of the IL-15:IL-15Rα complex, with both IL-15 peptide and the IL-15 receptor α-chain co-expressed in the same cell can stimulate immune effector cells bearing the IL-2βγC receptor through a trans-presentation mechanism. In addition, when IL-15 peptide is bound to IL-15Rα, affinity of the IL-15 peptide to IL-2Rβ increases approximately 150-fold compared with free IL-15. A superagonist mutant of IL-15 peptide (IL-15N72D) has increased IL-2Rβ binding ability (4-5 fold higher than native IL-15). The strong interaction of IL-15N72D and soluble IL-15Rα was exploited to create an IL-15 superagonist complex with IL-15N72D bound to IL-15RαSu. As an example, a superagonist complex may be an IL-15 derivative bound to an IL-15Rα/IgG1 Fc fusion protein, also known as nogapendekin alfa-imbakicept (NAI). NAI is also known in the literature as N-803, ALT-803, or IL-15$_{N72D}$:IL-15RαSu/IgG$_1$. U.S. Pat. No. 9,328,159, which describes NAI, is incorporated herein by reference in its entirety. Clinical trials involving N-803 are described in NCT04385849, which is incorporated herein by reference in its entirety.

Fusion Protein Complexes. The present disclosure provides a soluble fusion protein complex. The soluble fusion complex described herein comprises a first domain (e.g., an interleukin-15 (IL-15) peptide that may be an IL-15 variant (also referred to herein as IL-15 mutant, but also within the general scope of IL-15 peptide")), a second domain comprising a fusion polypeptide, and a third domain. The IL-15 peptide in the first domain preferably comprises a different amino acid sequence than the native (or wild type) IL-15 protein. The IL-15 peptide preferably binds the IL-15Rα peptide and functions as an IL-15 agonist or antagonist. Preferably, IL-15 peptides with agonist activity in the first domain may have super agonist activity. The IL-15 peptides can function as an IL-15 agonist or antagonist independent of its association with IL-15Rα. IL-15 agonists are exemplified by comparable or increased biological activity compared to wild type IL-15. IL-15 antagonists are exemplified by decreased biological activity compared to wild type IL-15 or by the ability to inhibit IL-15-mediated responses. In some examples, the IL-15 peptide in the first domain binds with increased or decreased activity to the IL-15RβγC receptors. In some cases, the sequence of the IL-15 peptide in the first domain has at least one amino acid change, e.g. substitution or deletion, compared to the native (or wildtype) humanIL-15 peptide, such changes resulting in IL-15 agonist or antagonist activity. Preferably, the amino acid substitutions/deletions are in the regions of IL-15 peptide that interact with IL-15Rβ and/or γC. More preferably, the amino acid substitutions/deletions do not affect binding to the IL-15Rα polypeptide or the ability to produce the IL-15 peptide. Suitable amino acid substitutions/deletions to generate IL-15 peptides in the first domain can be identified based on putative or known IL-15 structures, comparisons of IL-15 peptide with homologous molecules, such as IL-2, with known structures, through rational or random mutagenesis and functional assays, as provided herein, or other empirical methods. Additionally, suitable amino acid substitutions can be conservative or non-conservative changes and insertions of additional amino acids. Preferably, IL-15 peptides of the invention contain one or more than one amino acid substitutions/deletions at position 6, 8, 10, 61, 65, 72, 92, 101, 104, 105, 108, 109, 111, or 112 of the mature human IL-15 sequence; particularly, D8N ("D8" refers to the amino acid and residue position in the native mature human IL-15 sequence and "N" refers to the substituted amino acid residue at that position in the IL-15 variant), I6S, D8A, D61A, N65A, N72R, V104P or Q108A substitutions result in IL-15 peptides with antagonist activity and N72D substitutions result in IL-15 peptides with agonist activity. Alternative IL-15 peptides include those disclosed in U.S. Pat. Nos. 8,163,879 and 9,255,141, both of which are incorporated by reference in their entirety.

In some embodiments, the first domain may further comprises a first biologically active polypeptide covalently linked to interleukin-15 (IL-15) peptide or functional fragment thereof; and a second domain which comprises a second biologically active polypeptide covalently linked to soluble interleukin-15 receptor alpha (IL-15Rα) polypeptide or functional fragment thereof (e.g., IL15RαSu peptide), where the IL-15 peptide of the first domain binds to the soluble IL-15Rα peptide or functional fragment thereof of the second domain to form a soluble fusion protein complex. The fusion protein complexes may further comprise one or more immunoglobulin Fc peptides or a functional fragment thereof linked to one or both of the first and second domains. Additionally or alternatively, the Fc peptides linked to the first and/or second domains may interact to form a fusion protein complex. Such a complex may be stabilized by disulfide bond formation between the immunoglobulin Fc peptides. The soluble fusion protein complexes may include a first domain comprising an IL-15 peptide, (e.g., native or wildtype IL-15, an IL-15 variant, or a functional fragment thereof) and a second domain comprising soluble IL-15Rα polypeptide or a functional fragment thereof, wherein one or both of the IL-15 peptide and IL-15Rα polypeptide further include an immunoglobulin Fc domain or a functional fragment thereof.

Additionally or alternatively, one or both of the first and second domains may further comprise an antibody or functional fragment thereof. For example, one of the domains may comprise a soluble αCTLA4 single chain antibody variable fragment (scFv) or an αPD-L1 scFv or functional derivative thereof. By way of non-limiting example, suitable αCTLA4 antibodies are disclosed in WO 2021/250594, the entire contents of which are herein incorporated by reference. In another example, the first or second domain may comprise an αCTLA4 scFv or a disease antigen-specific antibody or functional derivative thereof. Examples of scFvs are disclosed in U.S. Pat. No. 11,105,188, which is incorporated herein by reference in its entirety. A soluble fusion protein complex that includes a covalently linked IL-15 peptide and IL-15Rα domains has several important uses. For example, the soluble fusion protein complex comprising an αCTLA4 scFv on the first or second domain may be employed to deliver the IL-15:IL-15Rα complex to certain cells, e.g., NK cells. Alternatively, as discussed below, the NK cells may include a high affinity NK cell which is engineered to express the fusion proteins. Accordingly, the protein fusion or conjugate complex provides means of selectively damaging or killing cells comprising the ligand. Examples of cells or tissue capable of being damaged or killed by the protein fusion or conjugate complexes include tumors and virally or bacterially infected cells expressing one or more ligands. Cells or tissue susceptible to being damaged or killed can be readily assayed by the methods disclosed herein.

Additionally or alternatively, the soluble fusion protein complex may further include a third domain, which may include another antibody or functional fragment thereof. For example, the third domain may comprise, for example an antibody light chain (e.g., an antibody fragment that does not comprise an Fc region). In a particular example, the third domain comprises an αCTLA4 antibody light chain, or a peptide having a sequence identity (e.g., at least about 85% sequence identity) to an αCTLA4 antibody light chain.

The IL-15 peptide and IL-15Rα peptide of the invention suitably correspond in amino acid sequence to naturally occurring IL-15 and IL-15Rα molecules, e.g. IL-15 and IL-15Rα molecules of a human, mouse or other rodent, or other mammals. Sequences of these polypeptides and encoding nucleic acids are known in the literature, including human interleukin 15 (IL-15) mRNA—GenBank: U14407.1 (incorporated herein by reference in its entirety), *Mus musculus* interleukin 15 (IL-15) mRNA—GenBank: U14332.1 (incorporated herein by reference in its entirety), human interleukin-15 receptor alpha chain precursor (IL-15Rα) mRNA—GenBank: U31628.1 (incorporated herein by reference in its entirety), *Mus musculus* interleukin 15 receptor, alpha chain—GenBank: BC095982.1 (incorporated herein by reference in its entirety).

In some settings, it can be useful to make the protein fusion or conjugate complexes of the present invention polyvalent, e.g., to increase the valency of the single chain-antibody. In particular, interactions between the IL-15 peptide and IL-15Rα peptide of the fusion protein complex provide a means of generating polyvalent complexes. In addition, the polyvalent fusion protein can be made by covalently or non-covalently linking together between one and four proteins (the same or different) by using e.g., standard biotin-streptavidin labeling techniques, or by conjugation to suitable solid supports such as latex beads. Chemically cross-linked proteins (for example cross-linked to dendrimers) are also suitable polyvalent species. For example, the protein can be modified by including sequences encoding tag sequences that can be modified such as the biotinylation BirA tag or amino acid residues with chemically reactive side chains such as Cys or His. Such amino acid tags or chemically reactive amino acids may be positioned in a variety of positions in the fusion protein, preferably distal to the active site of the biologically active polypeptide or effector molecule. For example, the C-terminus of a soluble fusion protein complex can be covalently linked to a tag or other fused protein which includes such a reactive amino acid(s). Suitable side chains may be included to chemically link two or more fusion proteins to a suitable dendrimer or other nanoparticle to give a multivalent molecule. Dendrimers are synthetic chemical polymers that can have any one of a number of different functional groups of their surface (D. Tomalia, *Aldrichimica Acta,* 26:91:101 (1993), incorporated herein by reference in its entirety). Exemplary dendrimers for use in accordance with the present invention include e.g. E9 starburst polyamine dendrimer and E9 combust polyamine dendrimer, which can link cysteine residues. Exemplary nanoparticles include liposomes, core-shell particles, or PLGA-based particles.

Additionally or alternatively, one or both of the first and second domains of the soluble fusion protein complex may comprise an immunoglobulin domain. Alternatively, the protein binding domain-IL-15 fusion protein may be further linked to an immunoglobulin domain. The immunoglobulin domains comprise regions that allow interaction with other immunoglobulin domains to form multichain proteins as provided above. For example, the immunoglobulin heavy chain regions, such as the IgG1 $C_H2$-$C_H3$, are capable of stably interacting to create the Fc region. Preferred immunoglobulin domains including Fc domains also comprise regions with effector functions, including Fc receptor or complement protein binding activity, and/or with glycosylation sites. In some aspects, the immunoglobulin domains of the fusion protein complex contain mutations that reduce or augment Fc receptor or complement binding activity or glycosylation or dimerization, thereby affecting the biological activity of the resulting protein. For example, immunoglobulin domains containing mutations that reduce binding to Fc receptors could be used to generate fusion protein complex of the invention with lower binding activity to Fc receptor-bearing cells, which may be advantageous for reagents designed to recognize or detect specific antigens.

Also described herein is a soluble fusion protein complex comprising a first domain comprising an IL-15 peptide, a second domain comprising a fusion polypeptide comprising an IL15RαSu peptide and an αCTLA4 antibody heavy chain, and a third domain comprising an αCTLA4 antibody light chain.

The IL-15 peptide may have at least about 75%, at least about 80% at least about 85%, at least about 90%, at least about 95%, at least about 96, at least about 97%, at least about 98%, or at least about 99% sequence identity to SEQ ID NO: 17, which does not include a leader sequence. The IL-15 peptide may comprise SEQ ID NO: 17. An exemplary nucleotide sequence encoding SEQ ID NO:17 is given herein as SEQ ID NO: 18. Alternatively, the IL-15 peptide may further include a leader sequence, and may have at least about 75%, at least about 80% at least about 85%, at least about 90%, at least about 95%, at least about 96, at least about 97%, at least about 98%, or at least about 99% sequence identity to SEQ ID NO: 1, which includes a leader sequence. The IL-15 peptide may comprise SEQ ID NO: 1. An exemplary nucleotide sequence encoding SEQ ID NO:1 is given herein as SEQ ID NO:2.

The IL15RαSu peptide may have at least about 75%, at least about 80% at least about 85%, at least about 90%, at least about 95%, at least about 96, at least about 97%, at least about 98%, or at least about 99% sequence identity to SEQ ID NO: 8. The IL15RαSu peptide may comprise SEQ ID NO: 8. The αCTLA4 antibody heavy chain may have at least about 75%, at least about 80% at least about 85%, at least about 90%, at least about 95%, at least about 96, at least about 97%, at least about 98%, or at least about 99% sequence identity to SEQ ID NO: 10. The αCTLA4 antibody heavy chain may comprise SEQ ID NO: 10. The αCTLA4 antibody light chain may have at least about 75%, at least about 80% at least about 85%, at least about 90%, at least about 95%, at least about 96, at least about 97%, at least about 98%, or at least about 99% sequence identity to SEQ ID NO: 3. The αCTLA4 antibody light chain may comprise SEQ ID NO: 3.

In particular, the soluble fusion protein complex may comprise first domain having an IL-15 peptide having at least about 85% sequence identity to SEQ ID NO: 17, a second domain having an IL15RαSu peptide and an αCTLA4 antibody heavy chain having at least about 85% sequence identity to SEQ ID NO: 10, and a third domain having an αCTLA4 antibody light chain having at least 85% sequence identity to SEQ ID NO: 3. The IL15RαSu peptide and the αCTLA4 antibody heavy chain may be part of a fusion polypeptide. The IL-15 peptide of the first domain may bind to the IL15RαSu peptide of the second domain to form a soluble fusion protein complex. The IL15RαSu peptide may have at least 85% sequence identity to SEQ ID NO: 8. Additionally or alternatively, the αCTLA4 antibody heavy and light chains may comprise complementarity determining regions (CDRs). The CDR regions of the αCTLA4 antibody heavy chain may have at least about 75%, at least about 80% at least about 85%, at least about 90%, at least about 95%, at least about 96, at least about 97%, at least about 98%, or at least about 99% sequence identity to one or more of SEQ ID NOs: 11-13. Alternatively, the CDR regions of the αCTLA4 antibody heavy chain may comprise each of SEQ ID NOs: 11-13. The CDR regions of the αCTLA4 antibody light chain may have at least about 75%, at least about 80% at least about 85%, at least about 90%, at least about 95%, at least about 96, at least about 97%, at least about 98%, or at least about 99% sequence identity to one or more of SEQ ID NOs: 14-16. Alternatively, the CDR regions of the αCTLA4 antibody light chain may comprise each of SEQ ID NOs: 14-16. In particular, the soluble fusion protein complex may comprise the αCTLA4 antibody heavy chain having at least about 90% sequence identity to SEQ ID NO: 10 and further comprise SEQ ID NOs: 11-13 and the αCTLA4 antibody light chain having about 90% sequence identity to SEQ ID NO: 3 and comprise SEQ ID NOs: 14-16. Alternatively, the soluble fusion protein complex may comprise the αCTLA4 antibody heavy chain having at least about 95% sequence identity to SEQ ID NO: 10 and further comprise SEQ ID NOs: 11-13 and the αCTLA4 antibody light chain having about 95% sequence identity to SEQ ID NO: 3 and comprise SEQ ID NOs: 14-16. Alternatively, the αCTLA4 antibody heavy chain of the soluble fusion protein complex comprises SEQ ID NO: 10 and the αCTLA4 antibody light chain comprises SEQ ID NO: 3.

The IL-15 peptide of the soluble fusion protein complex may or may not include a leader sequence. For example, the soluble fusion protein complex may comprise an IL-15 peptide lacking a leader sequence, wherein the IL-15 peptide comprises SEQ ID NO: 17. Alternatively, the soluble fusion protein complex may comprise an IL-15 peptide comprising a leader domain, wherein the IL-15 peptide comprises SEQ ID NO: 1.

The αCTLA4 antibody (e.g., the αCTLA4 antibody heavy chain) may be conjugated directly to the IL-15 peptide. Alternatively, the αCTLA4 antibody may be conjugated to an IL-15 receptor (e.g., IL15RαSu peptide), and the IL-15 peptide may associate with the anti-CTLA4/IL15RαSu chimera. Additionally or alternatively, the IL-15 peptide or IL15RαSu peptide may conjugated to the Fab end of the αCTLA4 antibody (e.g., the αCTLA4 antibody heavy chain), while in other embodiments the IL-15 peptide or IL15RαSu peptide may be conjugated to the Fc end of the αCTLA4 antibody heavy chain. The αCTLA4 antibody may be a full antibody or only an Fab fragment, while in other embodiments the αCTLA4 also includes an Fc domain. In certain embodiments, the αCTLA4 molecule is an IgA, IgE, IgG, or IgM antibody.

Additionally or alternatively, the soluble fusion protein complex may further comprise a peptide linker between one or more domains of the complex. For example, where the fusion polypeptide of the second domain of the soluble fusion protein complex comprises an IL15RαSu peptide and an αCTLA4 antibody heavy chain, the TL15RαSu peptide and the αCTLA4 antibody heavy chain may be directly conjugated via a peptide linker. The peptide linker may be between an amino terminus of the IL15RαSu peptide and a carboxy terminus of the αCTLA4 antibody heavy chain. In particular, the fusion polypeptide may have at least about 75%, at least about 80% at least about 85%, at least about 90%, at least about 95%, at least about 96, at least about 97%, at least about 98%, or at least about 99% sequence identity to SEQ ID NO: 5. Alternatively, the fusion polypeptide may comprise SEQ ID NO: 5.

Alternatively, the peptide linker may be between a carboxy terminus of the IL15RαSu peptide and an amino terminus of the αCTLA4 antibody heavy chain in the second domain. In particular, the fusion polypeptide may have at least about 75%, at least about 80% at least about 85%, at least about 90%, at least about 95%, at least about 96, at least about 97%, at least about 98%, or at least about 99% sequence identity to SEQ ID NO: 4. Alternatively, the fusion polypeptide may comprise SEQ ID NO: 4.

Amino acid mutations: There are several ways in which investigators have mutated the amino acid sequence of the IgG Fc region to modulate FcγR-based effector function. Some examples include point mutations, design algorithms, yeast display, and asymmetric engineering. The results from each of these different technologies have yielded numerous mutations that modify Fc-FcγR interactions and the resultant effector functions. For example, Fc-optimized immunoglobulin molecules based on amino acid substitutions are found to enhance ADCC. These include the following amino acid substitutions which increase FcγRIIIa binding: F243L/R292P/Y300L/V305I/P396L; S239D/I332E; S298A/E333A/K334A. Other mutations which have increased FcγRIIIa binding and decreased FcγRIIb binding are:239D/I332E/A330L. Other mutations with increased FcγRIIIa binding include in one heavy chain: L234Y/L235Q/G236W/S239M/H268D/D270E/S298A and in the opposing heavy chain: D270E/K326D/A330M/K334E (Xinhua & al. (2017) *Protein & Cell* 9(1):63-73, which is incorporated herein by reference in its entirety). Combining several identified mutations (e.g., S298A/E333A/K334A) resulted in enhanced ADCC relative to IgG1. A series of Fc variants with optimized Fcγ receptor affinity using computational design algorithms and high-throughput screening identified S239D/I332E and S239D/I332E/A330L as two variants with enhanced ADCC activity. A crystal structure of an Fc fragment with the mutations S239D/A330L/I332E was solved and modeling studies suggested that additional hydrogen bonds, hydrophobic contacts, and/or electrostatic interactions resulted in enhanced binding to FcγRIIIa. The addition of G236A to the S239D/I332E mutations resulted in up to 70-fold improved binding to FcγRIIa, a 13-fold improvement in the FcγRIIa/FcγRIIb binding ratio (activating/inhibitory ratio), and enhanced phagocytosis of antibody-coated target cells by macrophages. The variant F243L/R292P/Y300L/V305I/P396L, showed >100 fold increased ADCC activity (Stavenhagen & al. (2007) *Cancer Res.* 67:8882-90; which is incorporated herein by reference in its entirety). Antibody variants with an asymmetrically engineered Fc domain made by introducing different amino acid changes in each Fc domain demonstrated that L234Y/L235Q/G236W/S239M/H268D/D270E/S298A changes in one Fc domain and D270E/K326D/A330M/K334E changes in the other increased affinity for FcγRIIIa F158 by more than 2000-fold and FcγRIIIa V158 by more than 1000-fold (Mimoto & al. (2013) *MAbs.* 5:229-36; which is incorporated herein by reference in its entirety).

Glyco-engineering: IgGs contain a conserved glycosylation site at amino acid N297 in the CH2 domain. The core structure of the glycan is comprised of N-acetylglucosamine (GlcNAc) and mannose, where additional modifications can include bisecting GlcNAc, fucose, galactose, and sialic acid. One of the first reports linking glyco-engineering with enhanced Fc effector function demonstrated that IgG1 antibodies produced in a Chinese hamster ovary (CHO) cell line expressing β(1,4)-N-acetylglucosaminyltransferase III to express bisecting GlcNAc augmented ADCC activity relative to IgG1 (Umana & al. (1999) *Nat Biotechnol.* 17:176-80, which is incorporated herein by reference in its entirety). In addition, IgG1s deficient in fucose had an up to 50-fold increase in FcγRIIIa binding relative to IgG1 as well as enhanced ADCC (Shields & al. (2002) *J Biol Chem.* 277:26733-40, which is incorporated herein by reference in its entirety). It was later demonstrated that fucose deficient antibodies had improved ADCC function compared to antibodies containing bisecting GlcNAc (Shinkawa & al. (2003) *J Biol Chem.* 278:3466-73, which is incorporated herein by reference in its entirety). Amino acid N162 in FcγRIIIa contains a glycan, and the absence of fucose allows greater carbohydrate-carbohydrate interactions with the Fc, which increases the overall binding strength.

Antibody-Dependent Cell Cytotoxicity (ADCC): ADCC is the process by which antibodies coat a target cell and recruit effector cells to induce target cell death via non-phagocytic mechanisms. Antibodies can bind to their specific antigens on the target cell surface via their antigen-binding fragment (Fab) portions and interact with effector cells via their fragment crystallizable region (Fc) portions thereby acting as bridges that link the effector to a target. While several classes of human antibodies can mediate ADCC, including IgG, IgA, and IgE, IgG1 is the most used subclass for cancer therapeutic antibodies (Zahavi & al. (2018) *Antibody Therapeutics* 1(1):7-12, which is incorporated herein by reference in its entirety). In order for an effector cell to carry out ADCC, it must express Fc receptors (FcR) that will bind the antibody. The known classes of FcR include FcγR, which bind IgG; FcαR, which bind IgA; and FcεR, which bind IgE. Fcγ R are the most important for tumor cell clearance by myeloid cells and are comprised of activating Fcγ RI (CD64), Fcγ RIIA (CD32A), Fcγ RIIIA (CD16A), and inhibitory Fcγ RIIB (CD32B) receptors. Once the Fcγ R binds antibody it triggers receptor cross-linking and downstream signal propagation. Activating Fcγ R signal via their immunoreceptor tyrosine-based activation motifs while inhibitory Fcγ R signal via their immunoreceptor tyrosine-based inhibitory motifs. Many effector cells also express other receptor types such as the inhibitory killer inhibitory receptors (e.g. KIR) and activating NKG2D receptors on natural killer (NK) cells. The delicate balance amongst the activating and inhibitory pathway signaling ultimately determines effector cell response. Myeloid cells capable of acting as ADCC effectors are NK cells, monocytes, macrophages, neutrophils, eosinophils, and dendritic cells. Once these effector cells have been activated they mediate target cell death through three key mechanisms: cytotoxic granule release, Fas signaling, and elaboration of reactive oxygen species. The main and best characterized mechanism utilized in ADCC is the release of perforins and granzymes from effector cell granules. Upon activation, effector cells such as NK cells polarize and exocytose their granules in a calcium-dependent manner (de Saint Basile, G. & al. (2010) *Nat Rev Immunol.* 10:568-79, which is incorporated herein by reference in its entirety). Perforin and Granzyme B work in concert to induce cell death. Perforins create pores in the cell membrane that facilitate granzyme B entry into the target cell, resulting in DNA fragmentation and apoptosis. While multiple myeloid lineage cells are capable of ADCC, in the context of cancer immunotherapy NK cells appear to be the major effector cell type in vivo. The clinical efficacy of many targeted mAb therapies has been demonstrated to be NK cell dependent. NK cells highly express activating Fcγ RIIIA and do not express the inhibitory Fcγ RIIB; therefore modifying antibody interactions specifically through Fcγ RIIIA has become of interest for cancer immunotherapy.

High affinity NaturalKiller (haNK) Cells: NK-92 is a NK-like cell line that was initially isolated from the blood of a subject suffering from a large granular lymphoma and subsequently propagated in cell culture. The NK-92 cell line has been described (Klingemann & al. (2016) *Front Immunol* 7:91, which is incorporated herein by reference in its entirety). NK-92 cells determined have a CD3$^-$/CD56$^+$ phenotype that is characteristic of NK cells. They express all of the known NK cell-activating receptors except CD16, but lack all of the known NK cell inhibitory receptors except NKG2A/CD94 and ILT2/LIR1, which are expressed at low levels. Furthermore, NK-92 is a clonal cell line that, unlike the polyclonal NK cells isolated from blood, expresses these receptors in a consistent manner with respect to both type and cell surface concentration. Similarly, NK-92 cells are not immunogenic and do not elicit an immune rejection response when administered therapeutically to a human subject. Indeed NK-92 cells are well tolerated in humans with no known detrimental effects on normal tissues.

haNK cells are derived from the NK-92 cell line and have been engineered to express the high affinity CD16 allele. Sequences for high-affinity variants of the Fcγ receptor are well known in the art (see e.g., Bruhns & al. (2009) *Blood* 113:3716-25, which is incorporated herein by reference in its entirety). Expression of such receptor advantageously increases specific targeting and cytotoxic cell killing of tumor cells when using antibodies that are specific to a patient's tumor cells. CD16 is most commonly found in a form that has a relatively low binding affinity for the Fc portion of IgG molecules. An alternative form that exhibits a higher binding affinity is found in some individuals. The low and high affinity forms of CD16 differ only by the substitution of valine (high affinity) for phenylalanine (low affinity) at position 157 in the polypeptide chain. The complete sequences of the low and high affinity forms can be found in the SwissProt database as entries P08637 and VAR_008801, respectively.

Transduced NK-92 cells expressing CD16 on their surface (NK-92-CD16, also known as CD16/FcεRIγ-NK-92) are referred to herein as haNK. haNK cells expressing an antigen-binding, scFv are referred to herein as T-haNK cells.

Checkpoint Inhibitors: A checkpoint inhibitor inhibits the function or activity of a molecule that modulates or regulates, e.g., inhibits, immune response of an immune effector cell, e.g., T cell function. Inhibitory molecules, also referred to herein as checkpoint inhibitors, e.g., CTLA4, Programmed Death 1 (PD-1), can, in some embodiments, decrease the ability of an immune effector cell to mount an immune effector response. Examples of inhibitory molecules include PD-1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSFI4 or CD270), KIR, A2aR, MHC class I, MHC class II, GAL9, adenosine, and TGFR beta. Inhibition of a molecule that modulates or regulates, e.g., inhibits, T cell function, e.g., by inhibition at the DNA, RNA, or protein level, can optimize an immune response. In addition to the αCTLA4 antibodies disclosed herein, ipilimumab (also referred to as MDX-010 and MDX-101, and marketed as YERVOY™; Bristol-Myers Squibb) and tremelimumab (IgG2 monoclonal antibody available from Pfizer, formerly known as ticilimumab, CP-675,206) also bind to CTLA4.

Cytotoxic T-lymphocyte antigen 4 (CTLA4) is a member of a family of immunoglobulin-related receptors that are responsible for various aspects of T-cell immune regulation. The family includes CD28, CTLA4, and ICOS as well as other proteins, including PD-1, BTLA, and TIGIT. These receptors have both stimulatory (CD28, ICOS) and inhibitory roles (CTLA4, PD-1, BTLA, and TIGIT) in T-cell function. Increasingly, these pathways are targeted as part of immune modulatory strategies to treat cancers, referred to generically as immune checkpoint blockade, and conversely to treat autoimmunity and CTLA4 deficiency.

CTLA4 (CD152) and CD28 are homologous receptors expressed by both CD4$^+$ and CD8$^+$ T cells, which mediate opposing functions in T-cell activation. Both receptors share a pair of ligands expressed on the surface of antigen-presenting cells (APCs). CD28 interacts with the CD80 dimer with relatively high affinity and the CD86 monomer with lower affinity, mediating T-cell costimulation in conjunction with T-cell receptor (TCR) signals. In contrast, interactions of the ligands with CTLA4 serve to inhibit T-cell responses, although the precise mechanisms are not fully understood. CTLA4 interacts with both ligands with higher affinity and avidity than CD28 with CTLA4-CD80 forming the highest avidity interaction and CD28-CD86 forming the weakest interaction (Rowshanravan & al. (2018) *Blood* 131:58-67, which is incorporated herein by reference in its entirety). Among several possibilities, this raises the concept that CTLA4 can compete with CD28 for ligand binding and thereby act as an antagonist of CD28-mediated costimulation (Thompson & Allison (1997) *Immunity* 7(4):445-50; Walker & Sansom (2011) *Nat Rev Immunol.* 11(12):852-63, both of which are incorporated herein by reference in their entirety). These interactions are thought to take place at the immune synapse between T cells and APCs where CTLA4 has been shown to recruit CD80, thereby limiting its interactions with CD28 (Yokosuka & al. (2010) *Immunity* 33(3):326-39, which is incorporated herein by reference in its entirety).

Accordingly, in a method of treating cancer, a T-haNK cell can be engineered to express an anti-CTLA4 antigen binding domain, which binds to CTLA4 molecules with high affinity (Simpson & al. (2013) *J. Exp. Med.* 210(9): 1695-710, which is incorporated herein by reference in its entirety), leading to $T_{reg}$ cell depletion or functional blockade, resulting in enhanced T-cell activation and immunological responses to cancer.

CTLA4 is instrumental in mediating the suppressive functions of $T_{reg}$. Indeed, early experiments indicated that the major autoimmune phenotype of CTLA4-deficient mice could be prevented by the presence of CTLA4-expressing cells in mixed chimeras (Bachmann & al. (1999) *J Immunol.* 163(3):1128-31, which is incorporated herein by reference in its entirety). This observation has been supported by a number of other experiments (Walker & Sansom (2011)), and recently, a series of conditional and inducible CTLA4 deletion experiments have confirmed that the major phenotype is consistent with an effector function for CTLA4 on $T_{reg}$ (Klocke & al. (2016) *Proc Natl Acad Sci USA.* 113(17): E2383-92, which is incorporated herein by reference in its entirety).

In those embodiments wherein an autoimmune disease is to be treated, the T-haNK cells express CTLA4 resulting in an inhibition of immune response.

Immune cell activity that may be measured include, but is not limited to, (1) cell proliferation by measuring the DNA replication; (2) enhanced cytokine production, including specific measurements for cytokines, such as IFN-7, GM-CSF, or TNF-α; (3) cell mediated target killing or lysis; (4) cell differentiation; (5) immunoglobulin production; (6) phenotypic changes; (7) production of chemotactic factors or chemotaxis, meaning the ability to respond to a chemotactin with chemotaxis; (8) immunosuppression, by inhibition of the activity of some other immune cell type; and, (9) apoptosis, which refers to fragmentation of activated immune cells under certain circumstances, as an indication of abnormal activation.

Recombinant Expression Vectors and Host Cells: In general, preparation of the fusion protein complexes of the invention (e.g., components of a TxM complex) can be accomplished by procedures disclosed herein and by recognized recombinant DNA techniques.

In general, recombinant polypeptides are produced by transformation of a suitable host cell with all or part of a polypeptide-encoding nucleic acid molecule or fragment thereof in a suitable expression vehicle. Those skilled in the field of molecular biology will understand that any of a wide variety of expression systems may be used to provide the recombinant protein. The precise host cell used is not critical to the invention. A recombinant polypeptide may be produced in virtually any eukaryotic host (e.g., *Saccharomyces cerevisiae*, insect cells, e.g., Sf21 cells, or mammalian cells, e.g., NIH 3T3, HeLa, or preferably COS cells). Such cells are available from a wide range of sources (e.g., the American Type Culture Collection, Rockland, Md.; also, see, e.g., Ausubel & al., Current Protocol in Molecular Biology, New York: John Wiley and Sons, 1997, both of which are incorporated herein by reference in their entirety). The method of transfection and the choice of expression vehicle will depend on the host system selected. Transformation methods are described, e.g., in Ausubel & al. (supra); expression vehicles may be chosen from those provided, e.g., in Cloning Vectors: A Laboratory Manual (Pouwels & al., 1985, Supp. 1987, which is incorporated herein by reference in its entirety).

A variety of expression systems exist for the production of recombinant polypeptides. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

Once the recombinant polypeptide is expressed, it is isolated, e.g., using affinity chromatography. In one example, an antibody (e.g., produced as described herein)

raised against the polypeptide may be attached to a column and used to isolate the recombinant polypeptide. Lysis and fractionation of polypeptide-harboring cells prior to affinity chromatography may be performed by standard methods (see, e.g., Ausubel & al., supra). Once isolated, the recombinant protein can, if desired, be further purified, e.g., by high performance liquid chromatography (see, e.g., Fisher, Laboratory Techniques in Biochemistry and Molecular Biology, eds., Work and Burdon, Elsevier, 1980, which is incorporated herein by reference in its entirety).

Vectors are tools used to shuttle DNA between host cells or as a means to express a polynucleotide sequence. Inserting the DNA of interest, such as an scFv encoding an anti-CTLA4 binding domain, or a CD16 sequence or a fragment, is accomplished by ligation techniques and/or mating protocols well known to the skilled artisan. Such DNA is inserted such that its integration does not disrupt any necessary components of the vector. In the case of vectors that are used to express the inserted DNA as a polypeptide, the introduced DNA is operably-linked to the vector elements that govern its transcription and translation.

Vectors can be divided into two general classes: Cloning vectors are replicating plasmid or phage with regions that are non-essential for propagation in an appropriate host cell, and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA. In expression vectors, the introduced DNA is operably-linked to elements, such as promoters, that signal to the host cell to transcribe the inserted DNA. Some promoters are exceptionally useful, such as inducible promoters that control gene transcription in response to specific factors. Operably-linking an scFv encoding an αCTLA4 or a polynucleotide encoding a CTLA4 polypeptide to an inducible promoter can control the expression of a gene or fragments thereof. Examples of inducible promoters include those that are tissue-specific, which relegate expression to certain cell types, steroid-responsive (e.g., glucocorticoids, or heat-shock reactive. Other desirable inducible promoters include those that are not endogenous to the cells in which the construct is being introduced, but, however, are responsive in those cells when the induction agent is exogenously supplied.

Vectors have many manifestations. A "plasmid" is a circular double stranded DNA molecule that can accept additional DNA fragments. Viral vectors can also accept additional DNA segments into the viral genome. Certain vectors are capable of autonomous replication in a host cell (e.g., bacterial vectors having a bacterial origin of replication and episomal mammalian vectors). Other vectors (e.g., non-episomal mammalian vectors) integrate into the genome of a host cell and replicate as part of the host genome. In general, useful expression vectors are plasmids and viral vectors (e.g., replication defective retroviruses, adenoviruses and adeno-associated viruses); other expression vectors can also be used.

Vector choice is dictated by the organisms or cells being used and the desired fate of the vector. Vectors can replicate once in the target cells, or can be "suicide" vectors. In general, vectors comprise signal sequences, origins of replication, marker genes, enhancer elements, promoters, and transcription termination sequences. Vectors often use a selectable marker to facilitate identifying those cells that have incorporated the vector.

A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. A wide variety of host/expression vector combinations may be used to express the nucleic acid sequences described herein. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif), Stratagene (La Jolla, Calif.), and Invitrogen/Life Technologies (Carlsbad, Calif.).

Vectors can include, for example, origins of replication, scaffold attachment regions (SARs), and/or markers. A marker gene can confer a selectable phenotype on a host cell. For example, a marker can confer biocide resistance, such as resistance to an antibiotic (e.g., kanamycin, G418, bleomycin, or hygromycin). An expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or FLAG™ tag (Kodak, New Haven, CT) sequences typically are expressed as a fusion with the encoded polypeptide. Such tags can be inserted anywhere within the polypeptide, including at either the carboxyl or amino terminus.

Additional expression vectors also can include, for example, segments of chromosomal, non-chromosomal and synthetic DNA sequences. Suitable vectors include derivatives of SV40 and known bacterial plasmids, e.g., E. coli plasmids col El, pCR1, pBR322, pMal-C2, pET, pGEX, pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2p plasmid or derivatives thereof, vectors useful in eukaryotic cells, such as vectors useful in insect or mammalian cells; vectors derived from combinations of plasmids and phage DNAs, such as plasmids that have been modified to employ phage DNA or other expression control sequences.

Yeast expression systems can also be used. For example, the non-fusion pYES2 vector (XbaI, SphI, ShoI, NotI, GstXI, EcoRI, BstXI, BamHI, SacI, Kpn1, and HindIII cloning sites; Invitrogen) or the fusion pYESHisA, B, C (XbaI, SphI, ShoI, NotI, BstXI, EcoRI, BamHI, SacI, KpnI, and HindIII cloning sites, N-terminal peptide purified with ProBond resin and cleaved with enterokinase; Invitrogen), to mention just two, can be employed according to the invention. A yeast two-hybrid expression system can also be prepared in accordance with the invention.

Several delivery methods may be utilized for in vitro (cell cultures) and in vivo (animals and patients) systems. In one embodiment, a lentiviral gene delivery system may be utilized. Such a system offers stable, long term presence of the gene in dividing and non-dividing cells with broad tropism and the capacity for large DNA inserts. (Dull & al. (1998) *J Virol.* 72:8463-71, which is incorporated herein by reference in its entirety). In an embodiment, adeno-associated virus (AAV) may be utilized as a delivery method. AAV is a non-pathogenic, single-stranded DNA virus that has been actively employed in recent years for delivering therapeutic gene in in vitro and in vivo systems (Choi & al. *Curr Gene Ther* (2005) 5:299-310, which is incorporated herein by reference in its entirety). An example non-viral delivery method may utilize nanoparticle technology. This platform has demonstrated utility as a pharmaceutical in vivo. Nanotechnology has improved transcytosis of drugs across tight epithelial and endothelial barriers. It offers targeted delivery of its payload to cells and tissues in a specific manner (Allen & Cullis (1998) *Science,* 303:1818-22, which is incorporated herein by reference in its entirety).

The vector can also include a regulatory region. The term "regulatory region" may refer to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, nuclear localization signals, and introns.

The term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

Vectors include, for example, viral vectors (such as adenoviruses Ad, AAV, lentivirus, and vesicular stomatitis virus (VSV) and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Other vectors include those described by Chen & al. (2003) *BioTechniques* 34:167-71, which is incorporated herein by reference in its entirety. A large variety of such vectors is known in the art and are generally available. A "recombinant viral vector" refers to a viral vector comprising one or more heterologous gene products or sequences. Since many viral vectors exhibit size-constraints associated with packaging, the heterologous gene products or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying gene products necessary for replication and/or encapsidation). Modified viral vectors in which a polynucleotide to be delivered is carried on the outside of the viral particle have also been described (see, e.g., Curiel & al. (1991) *PNAS* 88:8850-54, which is incorporated herein by reference in its entirety).

Additional vectors include viral vectors, fusion proteins and chemical conjugates. Retroviral vectors include Moloney murine leukemia viruses and HIV-based viruses. One HIV based viral vector comprises at least two vectors wherein the gag and pol genes are from an HIV genome and the env gene is from another virus. DNA viral vectors include pox vectors such as orthopox or avipox vectors, herpesvirus vectors such as a herpes simplex I virus (HSV) vector [Geller & al. (1995) *J. Neurochem,* 64:487; Lim & al. (1995) in DNA Cloning: Mammalian Systems, D. Glover, Ed. (Oxford Univ. Press); Geller & al. (1993) *Proc Natl. Acad. Sci. USA* 90:7603; Geller & al. (1990) *Proc Natl. Acad. Sci USA* 87:1149], Adenovirus Vectors [LaSalle & al. (1993) *Science* 259:988; Davidson & al. (1993) *Nat. Genet.* 3:219; Yang & al. (1995) *J. Virol.* 69:2004] and Adeno-associated Virus Vectors [Kaplitt & al. (1994) *Nat. Genet.* 8:148], each of which are incorporated herein by reference in their entirety.

Since many viral vectors exhibit size-constraints associated with packaging, the heterologous gene products or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying gene products necessary for replication and/or encapsidation). Modified viral vectors in which a polynucleotide to be delivered is carried on the outside of the viral particle have also been described (see, e.g., Curiel, D T, & al. *PNAS* 88: 8850-8854, 1991, which is incorporated herein by reference in its entirety).

Suitable nucleic acid delivery systems include recombinant viral vector, typically sequence from at least one of an adenovirus, adenovirus-associated virus (AAV), helper-dependent adenovirus, retrovirus, or hemagglutinating virus of Japan-liposome (HVJ) complex. In such cases, the viral vector comprises a strong eukaryotic promoter operably linked to the polynucleotide e.g., a cytomegalovirus (CMV) promoter. The recombinant viral vector can include one or more of the polynucleotides therein, preferably about one polynucleotide. In some embodiments, the viral vector used in the invention methods has a pfu (plague forming units) of from about $10^8$ to about $5 \times 10^{10}$ pfu. In embodiments in which the polynucleotide is to be administered with a non-viral vector, use of between from about 0.1 nanograms to about 4000 micrograms will often be useful e.g., about 1 nanogram to about 100 micrograms.

Pox viral vectors introduce the gene into the cell cytoplasm. Avipox virus vectors result in only a short term expression of the nucleic acid. Adenovirus vectors, adeno-associated virus vectors and herpes simplex virus (HSV) vectors may be an indication for some invention embodiments. The adenovirus vector results in a shorter term expression (e.g., less than about a month) than adeno-associated virus, in some embodiments, may exhibit much longer expression. Suitable adenoviral vectors are disclosed in WO 09/06479 (Etubics Corp.), the entire contents of which are herein incorporated by reference in their entirety. The particular vector chosen will depend upon the target cell and the condition being treated. The selection of appropriate promoters can readily be accomplished. An example of a suitable promoter is the 763-base-pair cytomegalovirus (CMV) promoter. Other suitable promoters which may be used for gene expression include, but are not limited to, the Rous sarcoma virus (RSV) (Davis, & al., *Hum Gene Ther* 4:151 (1993), which is incorporated herein by reference in its entirety), the SV40 early promoter region, the herpes thymidine kinase promoter, the regulatory sequences of the metallothionein (MMT) gene, prokaryotic expression vectors such as the β-lactamase promoter, the tac promoter, promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells, insulin gene control region which is active in pancreatic beta cells, immunoglobulin gene control region which is active in lymphoid cells, mouse mammary tumor virus control region which is active in testicular, breast, lymphoid and mast cells, albumin gene control region which is active in liver, alpha-fetoprotein gene control region which is active in liver, alpha 1-antitrypsin gene control region which is active in the liver, beta-globin gene control region which is active in myeloid cells, myelin basic protein gene control region which is active in oligodendrocyte cells in the brain, myosin light chain-2 gene control region which is active in skeletal muscle, and gonadotropic releasing hormone gene control region which is active in the hypothalamus. Certain proteins can be expressed using their native promoter. Other elements that can enhance expression can also be included such as an enhancer or a system that results in high levels of expression such as a tat gene and tar element. This cassette can then be inserted into a vector, e.g., a plasmid vector such as, pUC19, pUC118, pBR322, or other known plasmid vectors, that includes, for example, an *E. coli* origin of replication. See, Sambrook, & al., Molecular Cloning: A Laboratory Manual, Cold Spring Harbor Laboratory press, (1989), which is incorporated herein by reference in its entirety. The plasmid vector may also include a selectable marker such as the β-lactamase gene for ampicillin resistance, provided that the marker polypeptide does not adversely affect the metabolism of the organism being treated.

Another delivery method is to use single stranded DNA producing vectors which can produce the expressed products intracellularly. The polynucleotides may be used with a microdelivery vehicle such as cationic liposomes and adenoviral vectors.

In certain embodiments of the invention, non-viral vectors may be used to effectuate transfection. Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386; 4,946,787; and 4,897,355, which are incorporated herein by reference in their entirety, and lipofection reagents are sold commercially (e.g., Transfectam and Lipofectin™). Cationic and neutral lipids that are suitable for efficient receptor-recognition lipofection of polynucleotides include those described in U.S. Pat. No. 7,166,298 or U.S. Pat. No. 6,890,554, the contents of each of which are incorporated by reference in their entirety. Delivery can be to cells (e.g. in vitro or ex vivo administration) or target tissues (e.g. in vivo administration).

Synthetic vectors are typically based on cationic lipids or polymers which can complex with negatively charged nucleic acids to form particles with a diameter in the order of 100 nm. The complex protects nucleic acid from degradation by nuclease. Moreover, cellular and local delivery strategies have to deal with the need for internalization, release, and distribution in the proper subcellular compartment. Systemic delivery strategies encounter additional hurdles, for example, strong interaction of cationic delivery vehicles with blood components, uptake by the reticuloendothelial system, kidney filtration, toxicity and targeting ability of the carriers to the cells of interest. Modifying the surfaces of the cationic non-virals can minimize their interaction with blood components, reduce reticuloendothelial system uptake, decrease their toxicity and increase their binding affinity with the target cells. Binding of plasma proteins (also termed opsonization) is the primary mechanism for RES to recognize the circulating nanoparticles. For example, macrophages, such as the Kupffer cells in the liver, recognize the opsonized nanoparticles via the scavenger receptor.

In some embodiments, delivery of vectors can also be mediated by exosomes. Exosomes are lipid nanovesicles released by many cell types. They mediate intercellular communication by transporting nucleic acids and proteins between cells. Exosomes contain RNAs, miRNAs, and proteins derived from the endocytic pathway. They may be taken up by target cells by endocytosis, fusion, or both. Exosomes can be harnessed to deliver nucleic acids to specific target cells.

The expression constructs of the present invention can also be delivered by means of nanoclews. Nanoclews are cocoon-like DNA nanocomposites (Sun & al. (2014) *J. Am. Chem. Soc.* 136:14722-25, which is incorporated herein by reference in its entirety). They can be loaded with nucleic acids for uptake by target cells and release in target cell cytoplasm. Methods for constructing nanoclews, loading them, and designing release molecules can be found in Sun & al. (2014) and Sun & al. (2015) *Angew. Chem. Int.* 2015:12029-33, which is incorporated herein by reference in its entirety.

The nucleic acids and vectors can be administered alone, or in a mixture, in the presence of a pharmaceutically acceptable excipient or carrier (e.g., physiological saline). The excipient or carrier is selected on the basis of the mode and route of administration. Suitable pharmaceutical carriers, as well as pharmaceutical necessities for use in pharmaceutical formulations, are described in Remington's Pharmaceutical Sciences (E. W. Martin), a well-known reference text in this field, and in the USP/NF (United States Pharmacopeia and the National Formulary).

In some embodiments of the invention, liposomes are used to effectuate transfection into a cell or tissue. The pharmacology of a liposomal formulation of nucleic acid is largely determined by the extent to which the nucleic acid is encapsulated inside the liposome bilayer. Encapsulated nucleic acid is protected from nuclease degradation, while those merely associated with the surface of the liposome is not protected. Encapsulated nucleic acid shares the extended circulation lifetime and biodistribution of the intact liposome, while those that are surface associated adopt the pharmacology of naked nucleic acid once they disassociate from the liposome. Nucleic acids may be entrapped within liposomes with conventional passive loading technologies, such as ethanol drop method (as in SALP), reverse-phase evaporation method, and ethanol dilution method (as in SNALP).

Liposomes and polymerosomes can contain a plurality of solutions and compounds. In certain embodiments, the complexes of the invention are coupled to or encapsulated in polymersomes. As a class of artificial vesicles, polymersomes are tiny hollow spheres that enclose a solution, made using amphiphilic synthetic block copolymers to form the vesicle membrane. Common polymersomes contain an aqueous solution in their core and are useful for encapsulating and protecting sensitive molecules, such as drugs, enzymes, other proteins and peptides, and DNA and RNA fragments. The polymersome membrane provides a physical barrier that isolates the encapsulated material from external materials, such as those found in biological systems. Polymerosomes can be generated from double emulsions by known techniques, see Lorenceau & al. (2005) *Langmuir* 21(20):9183-86, which is incorporated herein by reference in its entirety.

In some embodiments of the invention, non-viral vectors are modified to effectuate targeted delivery and transfection. PEGylation (i.e. modifying the surface with polyethyleneglycol) is the predominant method used to reduce the opsonization and aggregation of non-viral vectors and minimize the clearance by reticuloendothelial system, leading to a prolonged circulation lifetime after intravenous (i.v.) administration. PEGylated nanoparticles are therefore often referred as "stealth" nanoparticles. The nanoparticles that are not rapidly cleared from the circulation will have a chance to encounter infected cells.

In other embodiments, the compositions comprise an aNK cell which has been transformed or transfected with one or more vectors encoding the isolated nucleic acids embodied herein.

Transduced cells are prepared for reinfusion according to established methods. After a period of about 2-4 weeks in culture, the cells may number between $1 \times 10^6$ and $1 \times 10^{10}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent. For administration, cells of the present invention can be administered at a rate determined by the $LD_{50}$ of the cell type, and the side effects of the cell type at various concentrations, as applied to the mass and overall health of the patient. Administration can be accomplished via single or divided doses.

Pharmaceutical Therapeutics. In further embodiments, a pharmaceutical composition comprising the soluble fusion protein complex for use as a therapeutic is provided herein. The soluble fusion protein complex may be formulated with a pharmaceutically acceptable carrier to prepare the pharmaceutical composition. The pharmaceutical composition may be administered systemically, for example, formulated in a pharmaceutically acceptable buffer such as physiological saline. Preferable routes of administration include, for example, instillation into the bladder, subcutaneous, intravenous, intraperitoneal, intramuscular, intratumoral or intradermal injections that provide continuous, sustained, or effective levels of the composition in the patient. In particular, the soluble fusion protein complex and pharmaceutically acceptable carrier may be formulated for parenteral injection, including but not limited to subcutaneous, intravenous, intramuscular, intravesicular, intratumoral, or intraperitoneal injection.

Treatment of human patients or other animals is carried out using a therapeutically effective amount of a therapeutic identified herein in a physiologically acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia. Generally, amounts will be in the range of those used for other agents used in the treatment of other diseases associated with neoplasia, autoimmune or infectious diseases, although in certain instances lower amounts will be needed because of the increased specificity of the soluble fusion protein complex. A soluble fusion protein complex is administered at a dosage that enhances an immune response of a subject, or that reduces the proliferation, survival, or invasiveness of a neoplastic, infected, or autoimmune cell as determined by a method known to one skilled in the art.

Formulation of Pharmaceutical Compositions. The administration of the fusion protein complex of the invention for the prevention or treatment of a neoplasia, or autoimmune disease is by any suitable means that results in a concentration of the therapeutic that, combined with other components, is effective in ameliorating, reducing, or stabilizing said neoplasia, infectious or autoimmune disease. The fusion protein complex of the invention may be contained in any appropriate amount in any suitable carrier substance, and is generally present in an amount of 1-95% by weight of the total weight of the composition. The composition may be provided in a dosage form that is suitable for parenteral (e.g., subcutaneous, intravenous, intramuscular, intravesicular, intratumoral or intraperitoneal) administration route. For example, the pharmaceutical compositions are formulated according to conventional pharmaceutical practice (see, e.g., Remington: The Science and Practice of Pharmacy ($20^{th}$ ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York, which are incorporated herein by reference in their entirety).

Human dosage amounts are initially determined by extrapolating from the amount of the soluble fusion protein complex used in mice or non-human primates, as a skilled artisan recognizes it is routine in the art to modify the dosage for humans compared to animal models. For example, the dosage may vary from between about 1 µg soluble fusion protein complex/kg body weight to about 5000 mg complex/kg body weight; or from about 5 mg/kg body weight to about 4,000 mg/kg body weight or from about 10 mg/kg body weight to about 3,000 mg/kg body weight; or from about 50 mg/kg body weight to about 2000 mg/kg body weight; or from about 100 mg/kg body weight to about 1000 mg/kg body weight; or from about 150 mg/kg body weight to about 500 mg/kg body weight. For example, the dose is about 1, about 5, about 10, about 25, about 50, about 75, about 100, about 150, about 200, about 250, about 300, about 350, about 400, about 450, about 500, about 550, about 600, about 650, about 700, about 750, about 800, about 850, about 900, about 950, about 1,000, about 1,050, about 1,100, about 1,150, about 1,200, about 1,250, about 1,300, about 1,350, about 1,400, about 1,450, about 1,500, about 1,600, about 1,700, about 1,800, about 1,900, about 2,000, about 2,500, about 3,000, about 3,500, about 4,000, about 4,500, or about 5,000 mg/kg body weight. Alternatively, doses are in the range of about 5 mg complex/kg body weight to about 20 mg complex/kg body weight. In another example, the doses are about 8, about 10, about 12, about 14, about 16 or about 18 mg/kg body weight. Preferably, the soluble fusion protein complex is administered at about 0.5 mg/kg to about 10 mg/kg (e.g., about 0.5, about 1, about 3, about 5, about 10 mg/kg). Of course, this dosage amount may be adjusted upward or downward, as is routinely done in such treatment protocols, depending on the results of the initial clinical trials and the needs of a particular patient.

Pharmaceutical compositions are formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes. Preferably, the fusion protein complex is formulated in an excipient suitable for parenteral administration.

Parental Compositions. The pharmaceutical composition comprising a fusion protein complex of the invention may be administered parenterally by injection, infusion, or implantation (subcutaneous, intravenous, intramuscular, intratumoral, intravesicular, intraperitoneal) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions comprising a fusion protein complex of the invention for parenteral use are provided in unit dosage forms (e.g., in single-dose ampoules). Alternatively, the composition is provided in vials containing several doses and in which a suitable preservative may be added (see below). The composition is in the form of a solution, a suspension, an emulsion, an infusion device, or a delivery device for implantation, or it is presented as a dry powder to be reconstituted with water or another suitable vehicle before use. Apart from the active agent that reduces or ameliorates a neoplasia, infectious or autoimmune disease, the composition includes suitable parenterally acceptable carriers and/or excipients. The active therapeutic agent(s) may be incorporated into microspheres, microcapsules, nanoparticles, liposomes for controlled release. Furthermore, the composition may include suspending, solubilizing, stabilizing, pH-adjusting agents, tonicity adjusting agents, and/or dispersing, agents.

As indicated above, the pharmaceutical compositions comprising a soluble fusion protein complex of the invention may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl, or n-propyl p-hydroxybenzoate). In cases where one of the active therapeutics is only sparingly or slightly soluble in water, a dissolution enhancing or solubilizing agent can be added, or the solvent may include 10-60% w/w of propylene glycol.

The present invention provides methods of preventing or treating cancer, neoplasia, or autoimmune diseases or disorders, or symptoms thereof, comprising administering a therapeutically effective amount of a pharmaceutical composition comprising the soluble fusion protein complex to a subject (e.g., a mammal such as a human) in need thereof. Thus, one embodiment is a method of treating a subject suffering from or susceptible to a cancer, neoplasia, or autoimmune disease or disorder, or symptom thereof. In particular, the cancer treated by the administration of the pharmaceutical compositions includes acute leukemia, AIDS related cancer, breast cancer, bone cancer, brain cancer, cancers of the head and neck, lymphoma, adenoma, squamous cell carcinoma, laryngeal carcinoma, gallbladder and bile duct cancer, cancers of the retina, cancers of the esophagus, gastric cancer, multiple myeloma, ovarian cancer, uterine cancer, thyroid cancer, testicular cancer, endometrial cancer, melanoma, lung cancer, bladder cancer, prostate cancer, lung cancer, pancreatic cancer, sarcomas, Wilms' tumor, cervical cancer, skin cancers, nasopharyngeal carcinoma, liposarcoma, epithelial carcinoma, renal cell carcinoma, gallbladder adeno carcinoma, parotid adenocarcinoma, endometrial sarcoma, and multidrug resistant cancers. The method includes the step of administering to the mammal a therapeutic amount of the soluble fusion protein complex or a pharmaceutical composition comprising the soluble fusion protein complex described herein sufficient to treat the disease or disorder or symptom thereof, under conditions such that the disease or disorder is treated.

Additionally or alternatively, the described soluble fusion protein complex or a pharmaceutical composition containing the same may be used for preventing or treating cancer in a subject in need thereof. Additionally or alternatively, the described soluble fusion protein complex or a pharmaceutical composition containing the same may be used for preventing or treating autoimmune disease or disorder in a subject in need thereof.

The methods herein include administering to the subject (including a subject identified as in need of such treatment) an effective amount of the described soluble fusion protein complex or a pharmaceutical composition containing the same to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the soluble fusion protein complex described herein, such as a soluble fusion protein complex having a first domain having an IL-15 peptide having a sequence identity (e.g., at least an 85% sequence identity) to SEQ ID NO: 17, a second domain comprising a fusion polypeptide comprising an IL15RαSu peptide and an αCTLA4 antibody heavy chain having a sequence identity (e.g., at least an 85% sequence identity) to SEQ ID NO: 10, and a third domain having an αCTLA4 antibody light chain having a sequence identity (e.g., at least an 85% sequence identity) to SEQ ID NO: 3, wherein the IL-15 peptide of the first domain binds to the IL15RαSu peptide of the second domain to a subject (e.g., animal, human) in need thereof, including a mammal, particularly a human. Such treatment will be suitably administered to subjects, particularly humans, suffering from, having, susceptible to, or at risk for a neoplasia, infectious disease, autoimmune disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The fusion protein complexes of the invention may be used in the treatment of any other disorders In which an increase in an immune response is desired.

The invention also provides a method of monitoring treatment progress. The method includes the step of determining a level of diagnostic marker (Marker) (e.g., any target delineated herein modulated by the soluble fusion protein complex described herein, a protein or indicator thereof, etc.) or diagnostic measurement (e.g., screen, assay) in a subject suffering from or susceptible to a disorder or symptoms thereof associated with neoplasia in which the subject has been administered a therapeutic amount of the described soluble fusion protein complex sufficient to treat the disease or symptoms thereof. The level of Marker determined in the method can be compared to known levels of Marker in either healthy normal controls or in other afflicted patients to establish the subject's disease status. In some cases, a second level of Marker in the subject is determined at a time point later than the determination of the first level, and the two levels are compared to monitor the course of disease or the efficacy of the therapy. In certain aspects, a pre-treatment level of Marker in the subject is determined prior to beginning treatment according to this invention; this pre-treatment level of Marker can then be compared to the level of Marker in the subject after the treatment commences, to determine the efficacy of the treatment.

Combination Therapies. The soluble fusion protein complex described herein may be administered in combination with any other standard therapy; such methods are known to the skilled artisan and described in Remington's Pharmaceutical Sciences by E. W. Martin. If desired, a fusion protein complex of the invention may be administered in combination with any conventional anti-neoplastic therapy, including but not limited to, immunotherapy, therapeutic antibodies, targeted therapy, surgery, radiation therapy, or chemotherapy.

Kits or Pharmaceutical Systems. Pharmaceutical compositions comprising the fusion protein complex of the invention may be assembled into kits or pharmaceutical systems for use in ameliorating a neoplasia, or autoimmune disease. Kits or pharmaceutical systems according to this aspect of the invention comprise a carrier means, such as a box, carton, tube, having in close confinement therein one or more container means, such as vials, tubes, ampoules, bottles, and the like. The kits or pharmaceutical systems of the invention may also comprise associated instructions for using the fusion protein complex and/or cells of the invention.

EXAMPLES

Figure 2:
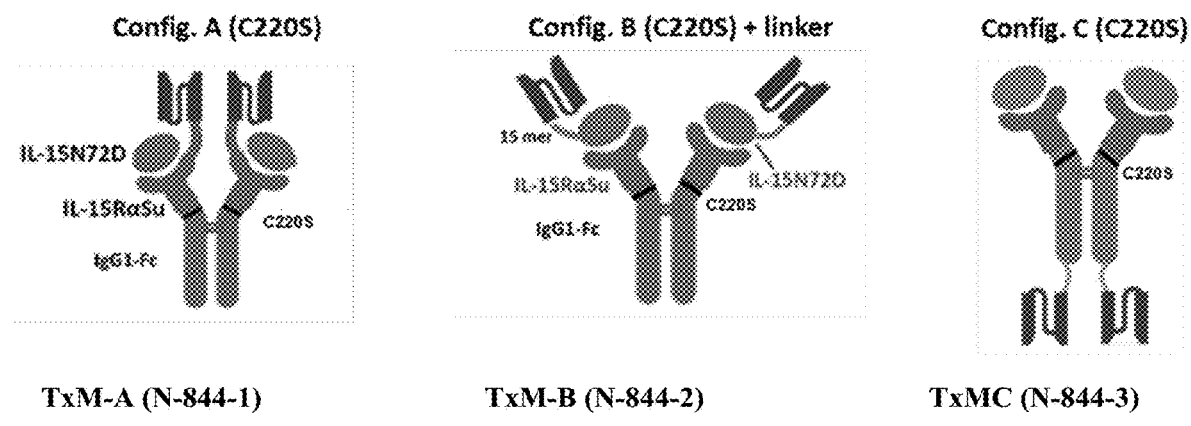
FIGS. 2 and 3 are to be interpreted, as well as two exemplary molecules illustrated according to this key.
Figure 3:
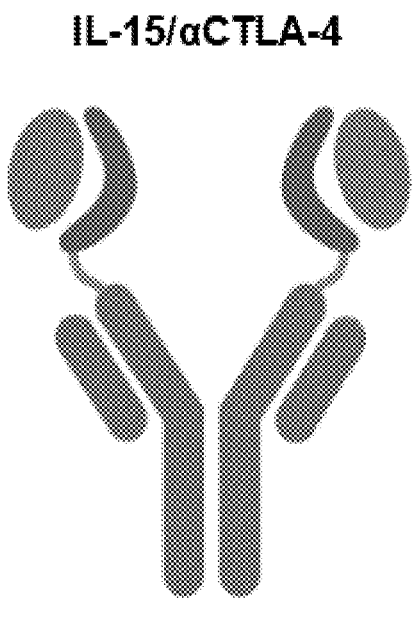
Figure 3:
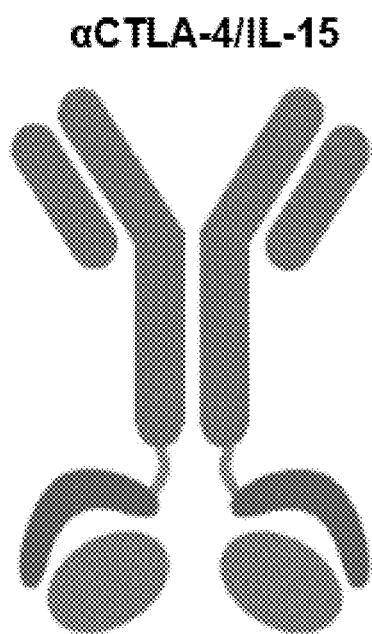

Example 1—Making Molecules as Shown in FIGS. 1-3

Molecules as shown in FIGS. 1-3 were made by transfecting mammalian cells to express the various molecules. One of skill in the art is well aware how to make a fusion protein complex and express a fusion protein complex in a mammalian cell. Briefly, DNA sequences encoding the soluble fusion protein complex were cloned into a mammalian expression vector under a CMV promoter with an SV40 polyadenylation sequence. The plasmid included ampicillin and puromycin resistance markers. The mammalian expression vector was transformed into chemically competent *E. coli*. The transformed *E. coli* were cultured under standard conditions in ampicillin-containing media. Plasmids were isolated and purified from the *E. coli* culture using a Qiagen Maxiprep® columns following manufacturer's protocol.

Chinese Hamster Ovary-S(CHO-S) cells were cultured in suspension in CD-CHO media supplemented with 8 mM L-glutamine in shaker flasks at 37° C. and 8% $CO_2$ and shaken at 125 rpm. For transfection, cells in the exponential growth stage were pelleted by centrifugation (1,400 rpm for 10 minutes), resuspended in 10 mL of electroporation buffer, and re-pelleted (1,400 rpm for 5 minutes). The cell pellet was resuspended at a density of $2 \times 10^8$ cells/mL in electroporation buffer mixed with the plasmid harboring the DNA sequence of interest at a DNA concentration of 150 µg/mL. The cells were transfected using OC-400 processing assemblies in a Maxcyte® ExPERT ATx Transfection System. Transfected cells were incubated for 30 minutes at 37° C. and 5% $CO_2$ and then resuspended in Efficient Feed A cocktail (CHO-CD EfficientFeed™ A +0.2% Pluronic F-68+ 1% HT supplement+1% L-glutamine) at a density of about $4-6 \times 10^6$ cells/mL. The cells were incubated on a shaker at 37° C. and 5% $CO_2$ and 125 rpm rotation overnight. 1 mM sodium butyrate was added and the culture was further incubated at 32° C., 3% $CO_2$ and 125 rpm for 13 additional days. Maxcyte® Feed Cocktail (13.9% CD hydrolysate, 69.5% CHO CD EfficientFeed™ A, 6.2% glucose, 6.9% FunctionMax™ Titer Enhancer, and 3.5% L-glutamine) was added at 10% of the culture volume on days 3 and 8. The culture was harvested on Day 14.

Titer of the fusion proteins was determined by obtaining a small aliquot of the cell culture supernatant following Maxcyte® transfection. The titer was measured using a Protein A biosensor (Sartorius) on an OctetRed96e instrument (Sartorius). The "% main peak" was determined after titer determination. A final elution pool after Protein A column purification or a second cation exchange column purification was analyzed on a size exclusion (SE) column (Sepax Zenix-C SEC-300) on HPLC (Agilent) equilibrated with 50 mM sodium phosphate, pH 6.8, 250 mM NaCl. The "% peak area" under the curve was calculated using the Agilent HPLC software. The purity analyses are shown in Table 1 below.

TABLE 1

| Fusion Protein | Titer (µg/mL) | % main peak on SE-HPLC | % main peak after second cation exchange column on SE-HPLC |
| --- | --- | --- | --- |
| αCTLA4/TxM-A (N-844-1) | 98.9 | 84.1% | 90.3% |
| αCTLA4/TxM-B (N-844-2) | 218.1 | 91.0% | 89.9% |
| αCTLA4/TxM-C (N-844-3) | 119.6 | 77.4% | 93.6% |
| IL-15/αCTLA4 (N-844-4) | 547.7 | 94.4% | 98.0% |
| αCTLA4/IL-15 (N-844-5) | 509.3 | 95.5% | 99.2% |

Example 2—Binding Assessment

Surface plasmon resonance (SPR) studies were conducted with the purified fusion proteins to assess their binding affinities to relevant targets. The SPR kinetic assay was performed by immobilizing rabbit α-human IgG Fc antibodies (Thermo) on a PCH sensor (Sartorius) as the capture molecule. All molecules of interest were then captured on the sensor surface by α-IgG1-Fc and Fc domain interaction. Binding kinetics against IL-2Rβ, human CTLA4, and murine CTLA4 were determined by OneStep injection at 40 nM and 20 nM of each analyte. The results of these studies are shown in Table 2 below. As can be seen in these data, αCTLA4/TxM-C's binding affinity against CTLA4 is reduced compared to A and B form indicating that the proximity of scFv at C-termini of Fc domain is detrimental to the structural integrity. The αCTLA4-scFv has higher affinity to CTLA4 than when the binding domain is in IgG form. All scFvs are formed in a VL-VH arrangement, although the orientation of VH and VL with respect to the linker does not appear to affect binding affinity.

TABLE 2

| Binding Target | Fusion protein | KD |
| --- | --- | --- |
| IL2RB | nogapendekin alfa-imbakicept (N-803) | 1.8-2.0 nM |
|  | αCTLA4/TxM-A (N-844-1) | 1.5 nM |
|  | αCTLA4/TxM-B (N-844-2) | 3.1 nM |
|  | αCTLA4/TxM-C (N-844-3) | 1.3 nM |
|  | IL-15/αCTLA4 (N-844-4) | 1.7 nM |
|  | αCTLA4/IL-15 (N-844-5) | 1.9 nM |
| Human CTLA4 | αCTLA4-7 | 1.1-1.6 nM |
|  | αCTLA4/TxM-A (N-844-1) | 0.3-0.6 nM |
|  | αCTLA4/TxM-B (N-844-2) | 0.1-0.9 nM |
|  | αCTLA4/TxM-C (N-844-3) | 1.7-3.9 nM |
|  | IL-15/αCTLA4 (N-844-4) | 1.2-1.3 nM |
|  | αCTLA4/IL-15 (N-844-5) | 1.2-1.4 nM |
| Mouse CTLA4 | αCTLA4-7 | 0.13-2.1 nM |
|  | αCTLA4/TxM-A (N-844-1) | 0.1 nM |
|  | αCTLA4/TxM-B (N-844-2) | 0.1-0.2 nM |
|  | αCTLA4/TxM-C (N-844-3) | 0.3-1.1 nM |
|  | IL-15/αCTLA4 (N-844-4) | 2.0-3.4 nM |
|  | αCTLA4/IL-15 (N-844-5) | 2.1-2.6 nM |

Example 3—Stability Assessment

Figure 4:
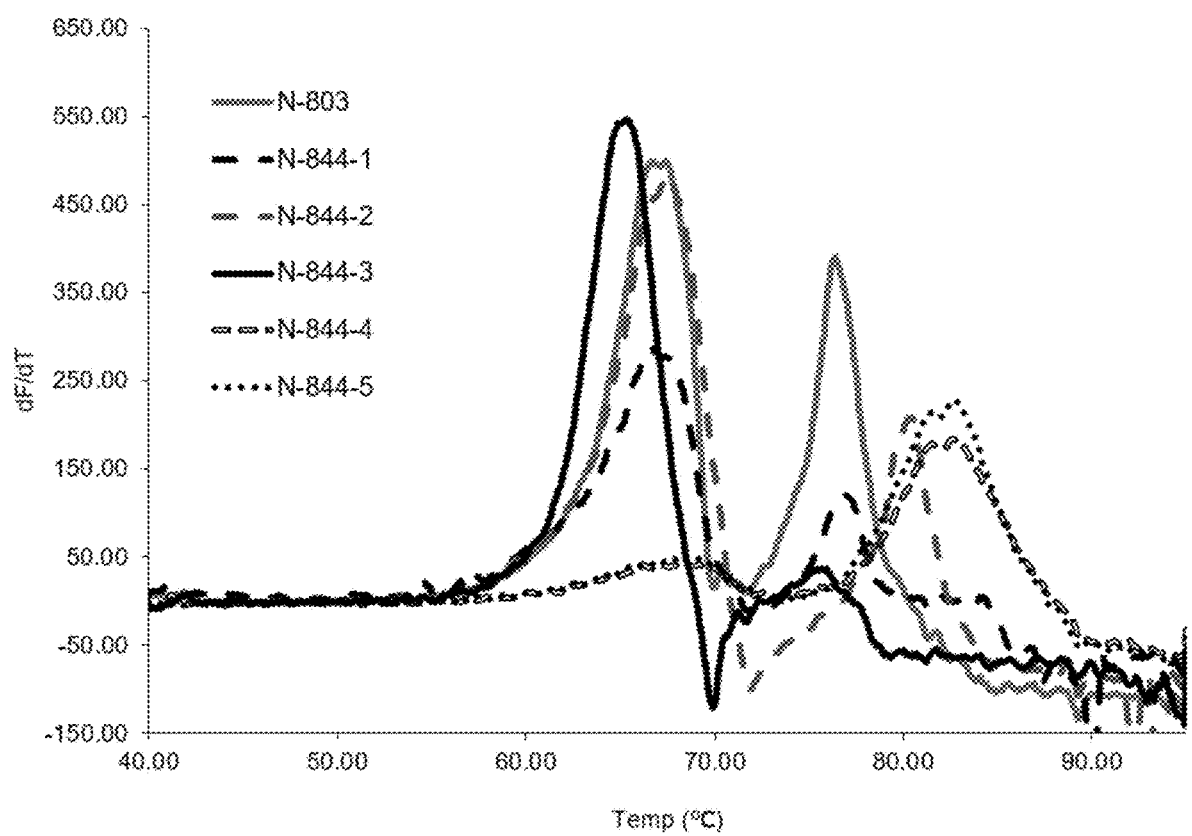
FIG. 4 is a graphical representation of a differential scanning fluorimetry Tm analysis of the various molecules shown in FIGS. 2 & 3 (nogapendekin alfa-imbakicept (also known as NAI or ALT-803) (N-803); α-CTLA4-TxM-A (N-844-1); α-CTLA4-TxM-B (N-844-2); α-CTLA4-TxM-C(N-844-3); IL-15-α-CTLA4 (N-844-4); α-CTLA4-IL-15 (N-844-5)).

In order to assess the stability of the various configurations of fusion proteins, the purified fusion proteins were analyzed by differential scanning fluorimetry (DSF). 20 μL of 1 mg/mL ACEIgG1Fc was mixed with 10 μL of SYPRO orange in appropriate wells or a plate. The plate was scanned from 25° C. to 70° C. (0.5° C. increment) on a CFX96 Real-Time System (BioRad). The results are shown in FIG. 4. As can be seen, the molecules of FIG. 3 are intrinsically more stable than those of FIG. 2.

Example 4—Off-Target Effects Assessment

Useful therapeutic candidates must not only specifically bind to target, but should also not exhibit off-target effects. The various molecular configurations were examined according to a number of assays for off-target effects. The general method for determining off target effects can be found in Jain & al. (2017) *Proc. Natl. Acad. Sci. USA* 114:944-949, which is incorporated herein by reference in its entirety Cetuximab was included in the tests as a negative control, while an αIL-18 antibody (43-12b) serves as a positive control antibody. The results are shown in Table 3 below. MSD-polyreactivity assays (Column A) test for non-specific stickiness, which is often indicative of faster clearance in monoclonal antibodies. Hydrophobic interaction chromatography (HIC) (Column B) measures monoclonal antibodies' hydrophobicity, a likely correlate with aggregation-proneness. Clone self-interaction using bio-layer interferometry (CSI-BLI) (Column C) measures the tendency of monoclonal antibodies to autoaggregate, which is often indicative of low solubility. Accelerated stability (Column D) measures the long-term aggregation propensity of a monoclonal antibody. Based on these results, αLCTLA4/TxM-B and both αLCTLA4/IL-15 fusions are all strong candidates.

TABLE 3

| Sample ID | A. Fold-over-PBS (nm) | B. Elution time (min) | C. Average (nm) | D. % loss monomer/day |
| --- | --- | --- | --- | --- |
| αCTLA4/TxM-A (N-844-1) | 21 | 14.0 | 0.02 | −0.03 |
| αCTLA4/TxM-B (N-844-2) | 2 | 14.1 | 0.01 | 0.05 |
| αCTLA4/TxM-C (N-844-3) | 3 | 12.9 | −0.10 | 0.31 |
| IL-15/αCTLA4 (N-844-4) | 8 | 12.4 | −0.06 | not tested |
| αCTLA4/IL-15 (N-844-5) | 3 | 12.6 | −0.10 | not tested |
| αCTLA4-7 | 19 | 12.2 | 0.12 | not tested |
| nogapendekin alfa-imbakicept (N-803) | 9 | 10.8 | −0.06 | not tested |
| αPD-L1 antibody (N-601) | 3 | 14.0 | 0.05 | 0.19 |
| Cetuximab | 4 | 13.9 | 0.00 | 0.18 |
| αIL-8 antibody (43-12b) | 165 | 21.3 | 0.29 | 0.43 |

Example 5—B16.F10 Melanoma Tumor Model

Figure 5:
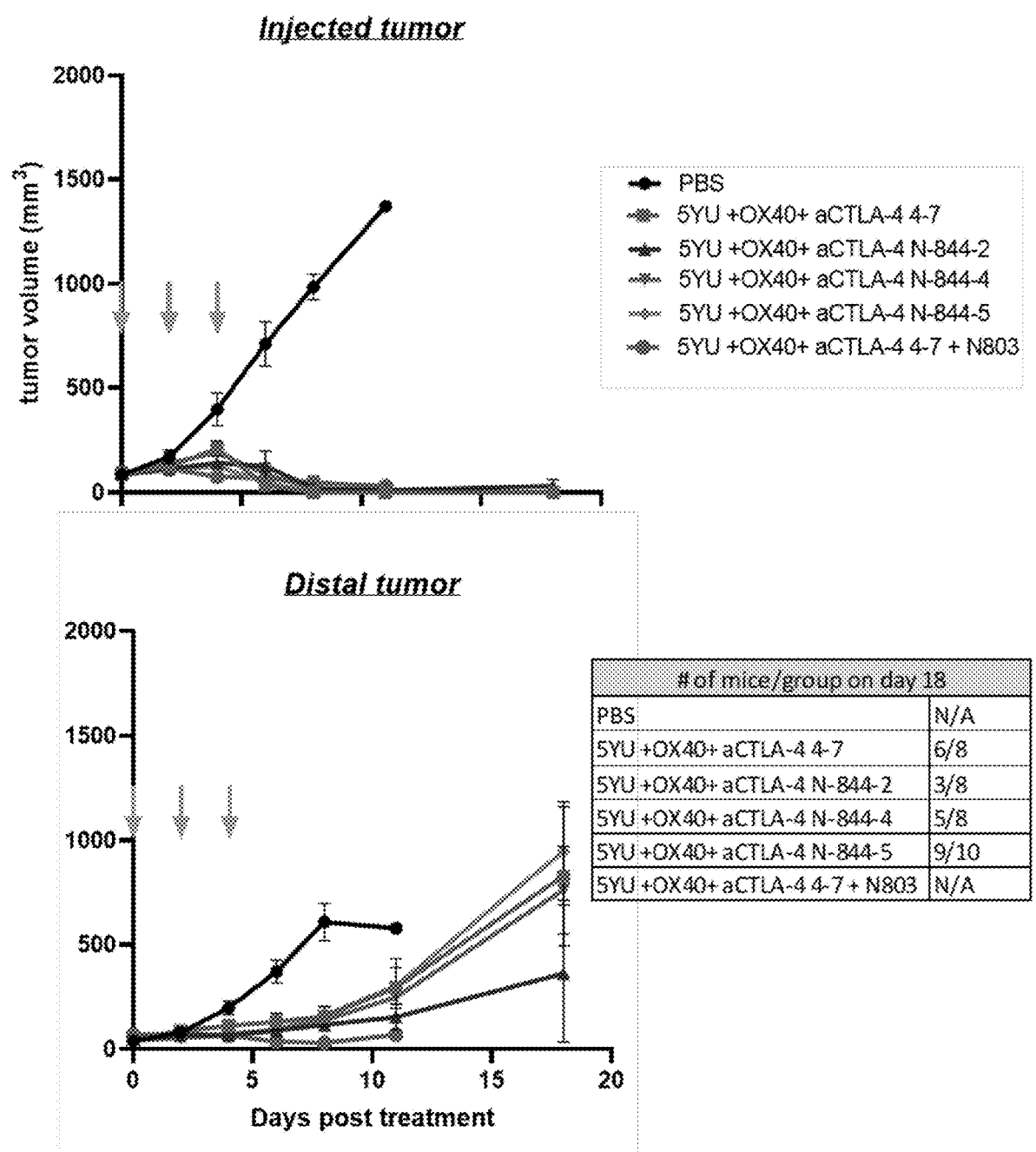
FIG. 5 is a graphical representation of average tumor growth in mice inoculated with B16.F10 melanoma tumor cells in both flanks. Treatments were provided directly to a tumor on one flank ("injected tumor"). Tumor growth was monitored in both the injected tumor and the uninjected tumor on the other flank ("distal tumor).
Figure 6A:
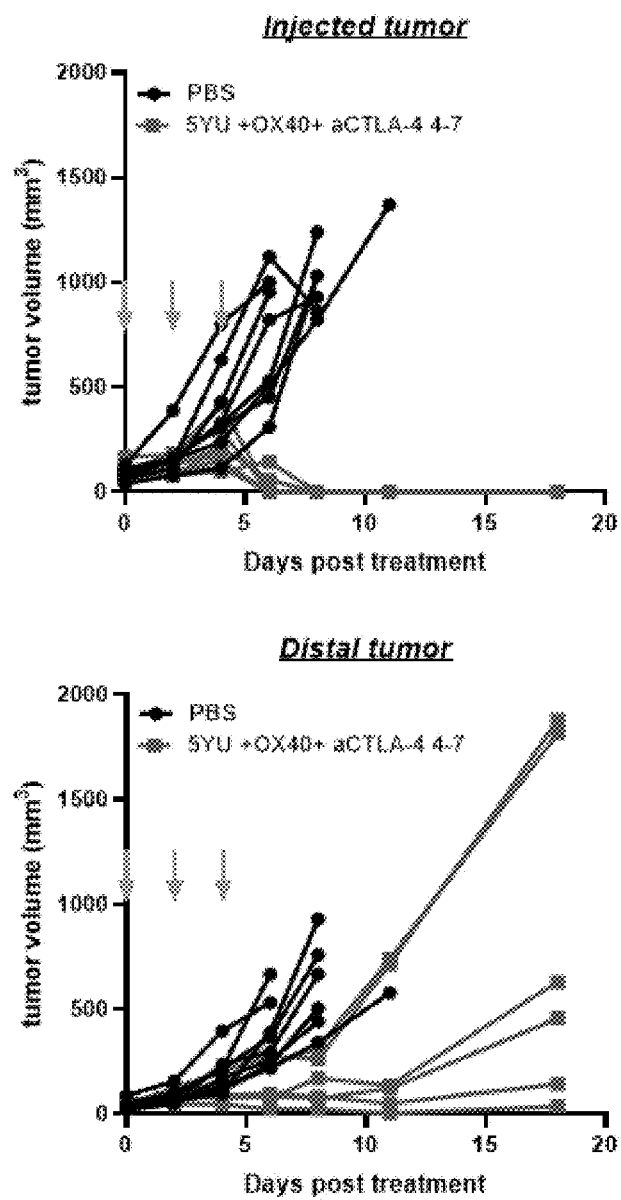
FIGS. 6A-6E is a graphical representation of tumor growth in the individual mice aggregated in FIG. 5.
Figure 6B:
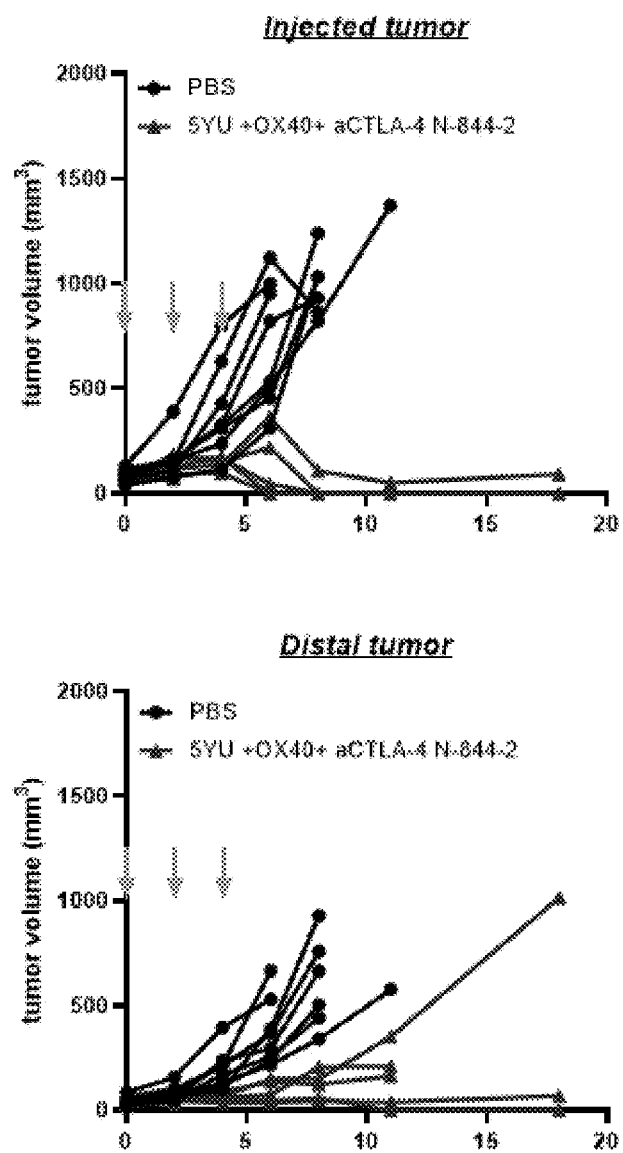
Figure 6C:
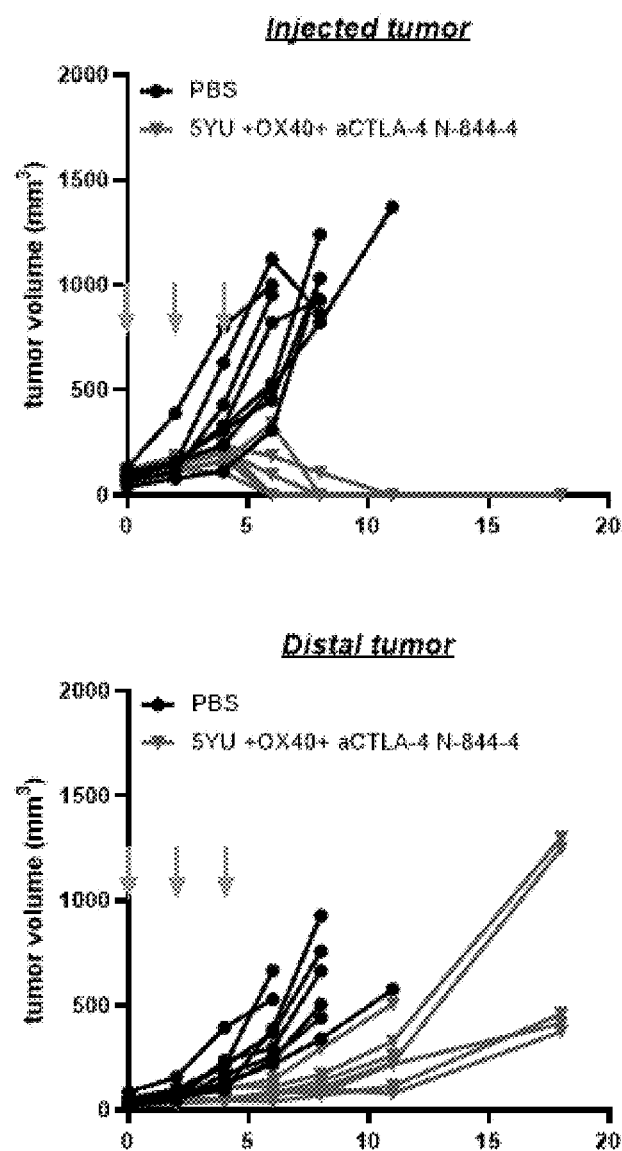
Figure 6D:
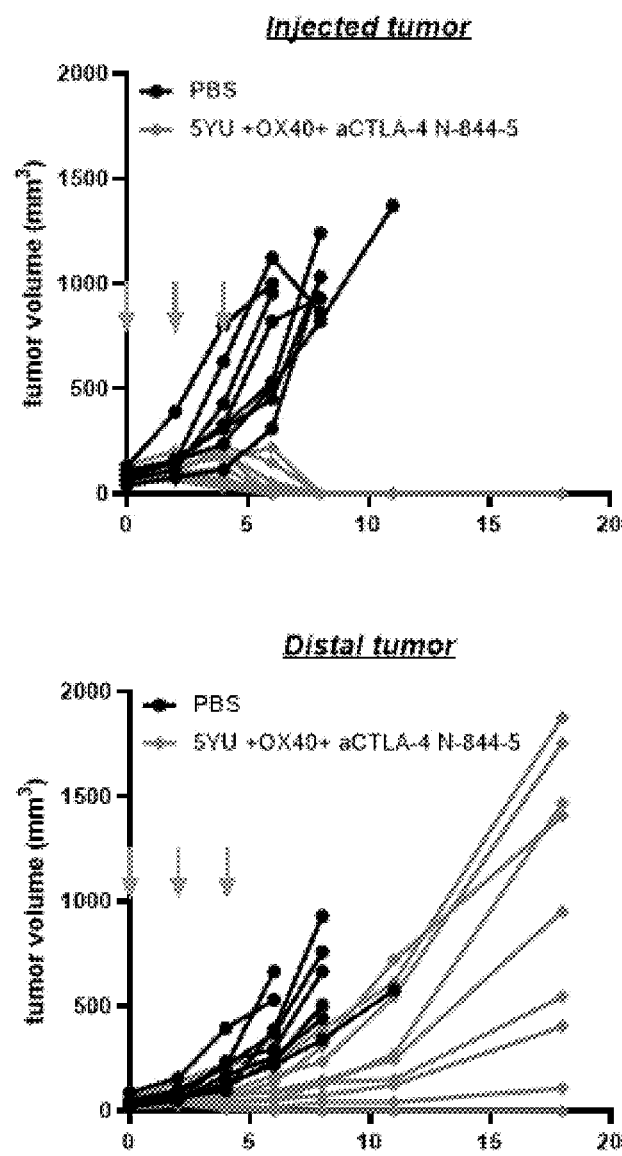
Figure 6E:
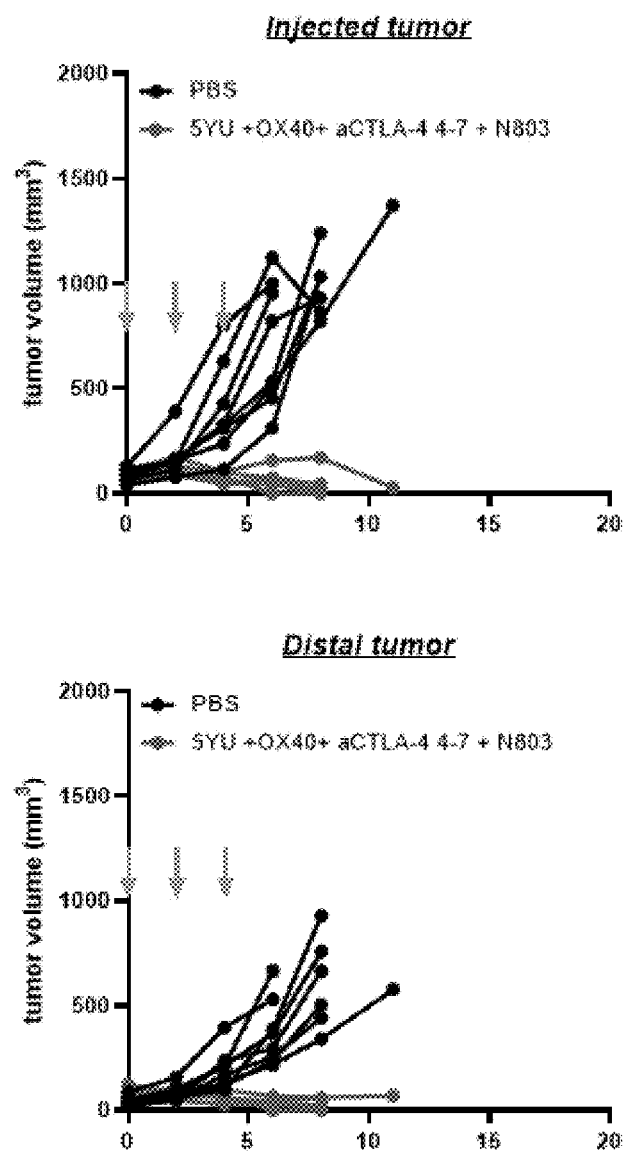
Figure 7A:
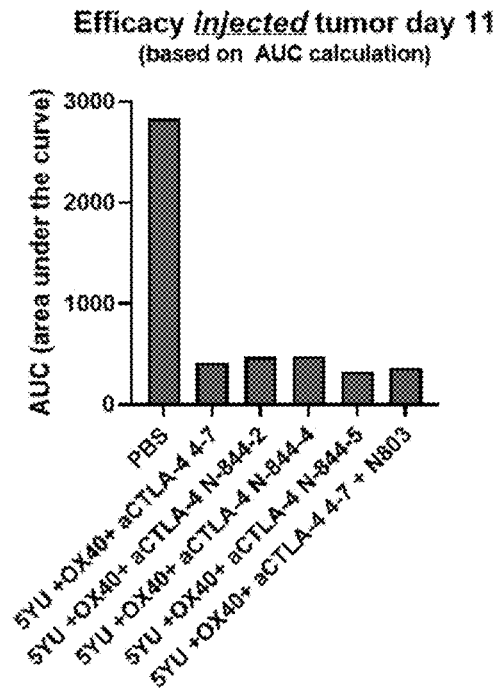
FIGS. 7A-C is a graphical representation of the efficacy of treatment in the injected and distal tumors on Day 11 based on area under the curve (AUC) calculation.
Figure 7B:
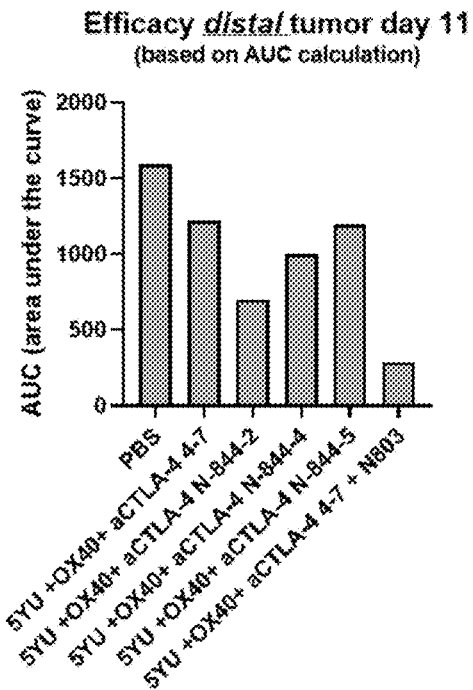
Figure 7C:
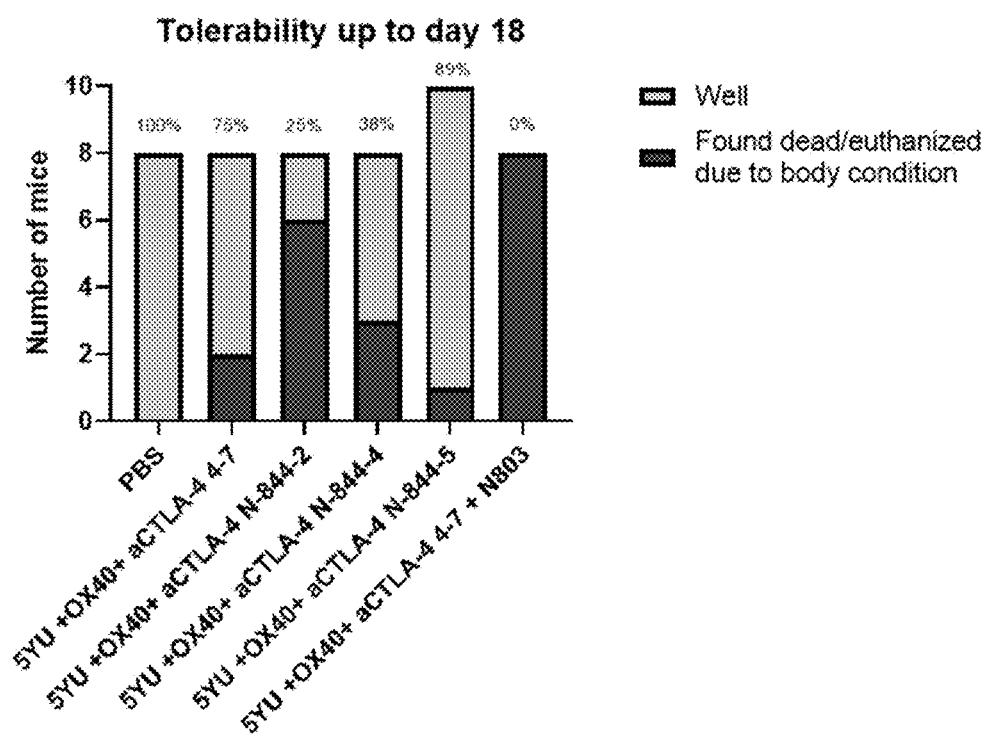

The syngeneic B16.F10 melanoma tumor model was used for preclinical evaluation of these candidate immunotherapies by intratumoral (i.t.) administration. C57BL/6 mice were purchased from the Jackson Laboratories (Maine, USA). The B16.F10 murine melanoma cell line was maintained as monolayers in culture using RPMI medium supplemented with 10% heat-inactivated fetal bovine serum (FBS), 100 non-essential amino acids, 10 mM TBEPES, 10% Sodium Pyruvate, and 10% Penicillin/Streptomycin. Single-cell suspensions of B16.F10 monolayers were generated and $1.3 \times 10^5$ cells in a 50 μL volume of PBS were implanted intradermally into each of the left and right shaved flanks of C57BL/6 mice. Tumors were allowed to grow until they reached an average diameter of 5-7 mm (about 8 days) upon which mice were randomly enrolled into treatment groups. For each mouse, the larger of the two tumors was injected on day 0, 2, and 4 post enrollment with a 50 μL total volume of the treatment indicated. The i.t. treatments consisted of PBS (as a negative control) or 5 yeast units (YU, 1YU=$10^7$ cells) of *Saccharomyces cerevisiae* yeast lysate expressing 4 B16.F10 neoepitopes, 25 g anti-OX40 antibody, and one of: 25 μg αCTLA4-7; 25 μg αCTLA4-7+25 μg NAI (N-803); 25 μg αCTLA4/TxM-B (N-844-2); 25 μg IL-15/αCTLA4 (N844-4); or 25 μg αCTLA4/IL-15 (N-844-5). Both the treated (injected) and untreated (distal) tumors were measured at periodic intervals using a digital caliper, and the longest diameter (A) and the shorter diameter (B) were used to calculate the tumor volume as V=(AB²)/2. Tumor growth was monitored over time, and mice euthanized when tumors reached ≥1000 mm³ volume. The aggregated results of are shown in FIG. 5. The tumor growths in individual mice are shown in FIGS. 6A-6E. Efficacy of the treatments in the injected and distal tumors on Day 11, as measured by an AUC calculation, are shown in FIGS. 7A and 7B, respectively. The results show that administration of the soluble fusion protein complexes significantly reduces tumor volume. FIG. 7C shows that the described soluble fusion protein complexes are generally tolerated up to 18 days in the murine melanoma model.

Example 6—pSTAT5 Assay

The function of the recited soluble fusion protein complex is measured by an in vitro staining assay. IL-2-starved aNK cells (4×10⁵ cells/wells in each well of a 96-well plate) are stimulated with a dilution series of an IL-18/IL-15/IL-12 superkine (8-points of 10-fold dilutions, starting from 100 nM). Following stimulation, the cells are fixed, permeabilized, and stained by PE-labeled αpSTAT5. PE-stained aNK cells are detected and quantified via intracellular flow cytometry. The data is processed with a GraphPad Prism to determine EC₅₀ for superkine stimulation.

All references, including publications, patent applications, and patents, cited herein are hereby incorporated by reference to the same extent as if each reference were individually and specifically indicated to be incorporated by reference and were set forth in its entirety herein.

The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Particular embodiments of this invention are described herein, including the best mode known to the inventors for carrying out the invention. Variations of those particular embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

TABLE 4

| SEQ ID NO: | Description | Sequence |
|---|---|---|
| 1 | IL-15 N72D mutant with leader peptide (AA) | METDTLLLWV LLLWVPGSTG NWVNVISDLK KIEDLIQSMH IDATLYTESD VHPSCKVTAM KCFLLELQVI SLESGDASIH DTVENLIILA NDSLSSNGNV TESGCKECEE LEEKNIKEFL QSFVHIVQMF INTS |
| 2 | IL15 N72D mutant with leader peptide (DNA) | atggagacag acacactcct gttatgggta ctgctgctct gggttccagg ttccaccggt aactgggtga atgtaataag tgatttgaaa aaaattgaag atcttattca atctatgcat attgatgcta ctttatatac ggaaagtgat gttcacccca gttgcaaagt aacagcaatg aagtgctttc tcttggagtt acaagttatt tcacttgagt ccggagatgc aagtattcat gatacagtag aaaatctgat catcctagca aacgacagtt tgtcttctaa tgggaatgta acagaatctg gatgcaaaga atgtgaggaa ctggaggaaa aaaattattaa agaattttg cagagttttg tacatattgt ccaaatgttc atcaacactt cttaa |
| 3 | Anti-CTLA4 light chain | DIQMTQSPSS LSASVGDRVT ITCQASQDIS NYLNWYQQKP GKAPKLLIYD ASNLETGVPS RFSGSGSGTD FTFTISSLQP EDIATYYCQQ GDAWPWTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 4 | N-terminal sushi domain fusion with anti-CTLA4 heavy chain | ITCPPPMSVE HADIWVKSYS LYSRERYICN SGFKRKAGTS SLTECVLNKA TNVAHWTTPS LKCIRGGGGS GGGGSGGGGS EVQLVESGGG LVQPGGSLRL SCAASGFTFT SYSMHWVRQZ PGKGLEWVSG ISGSGRSTSY ADSVKGRFTI SRDNSKNTLY LQMNSLRAED TAVYYCARDL MAFNLVRAGG FDVWGQGTLV TVSSASTKGP SVFPLAPSSK STSGGTAALG CLVKDYFPEP VTVSWNSGAL TSGVHTFPAV LQSSGLYSLS SVVTVPSSSL GTQTYICNVN HKPSNTKVDK KVEPKSCDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SRDELTKNQV SLTCLVKGFY PSDIAVEWES NGQPENNYKT |

TABLE 4-continued

| SEQ ID NO: | Description | Sequence |
|---|---|---|
| | | TPPVLDSDGS FFLYSKLTVD KSRWQQGNVF SCSVMHEALH NHYTQKSLSL SPGK |
| 5 | C-terminal sushi domain fusion with anti-CTLA4 heavy chain | EVQLVESGGG LVQPGGSLRL SCAASGFTFT SYSMHWVRQA PGKGLEWVSG ISGSGRSTSY ADSVKGRFTI SRDNSKNTLY LQMNSLRAED TAVYYCARDL MAFNLVRAGG FDVWGQGTLV TVSSASTKGP SVFPLAPSSK STSGGTAALG CLVKDYFPEP VTVSWNSGAL TSGVHTFPAV LQSSGLYSLS SVVTVPSSSL GTQTYICNVN HKPSNTKVDK KVEPKSCDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SRDELTKNQV SLTCLVKGFY PSDIAVEWES NGQPENNYKT TPPVLDSDGS FFLYSKLTVD KSRWQQGNVF SCSVMHEALH NHYTQKSLSL SPGKGGGGSG GGGSGGGGSI TCPPPMSVEH ADIWVKSYSL YSRERYICNS GFKRKAGTSS LTECVLNKAT NVAHWTTPSL KCIR |
| 6 | Anti-CTLA4 scFv-sushi-Fc | DIQMTQSPSS LSASVGDRVT ITCQASQDIS NYLNWYQQKP GKAPKLLIYD ASNLETGVPS RFSGSGSGTD FTFTISSLQP EDIATYYCQQ GDAWPWTFGQ GTKVEIKGGG GSGGGGSGGG GSEVQLVESG GGLVQPGGSL RLSCAASGFT FTSYSMHWVR QAPGKGLEWV SGISGSGRST SYADSVKGRF TISRDNSKNT LYLQMNSLRA EDTAVYYCAR DLMAFNLVRA GGFDVWGQGT LVTVSSITCP PPMSVEHADI WVKSYSLYSR ERYICNSGFK RKAGTSSLTE CVLNKATNVA HWTTPSLKCI REPKSSDKTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS RDELTKNQVS LTCLVKGFYP SDIAVEWESN GQPENNYKTT PPVLDSDGSF FLYSKLTVDK SRWQQGNVFS CSVMHEALHN HYTQKSLSLS PGK |
| 7 | Anti-CTLA4 scFv-IL-15 (N72D) | DIQMTQSPSS LSASVGDRVT ITCQASQDIS NYLNWYQQKP GKAPKLLIYD ASNLETGVPS RFSGSGSGTD FTFTISSLQP EDIATYYCQQ GDAWPWTFGQ GTKVEIKGGG GSGGGGSGGG GSEVQLVESG GGLVQPGGSL RLSCAASGFT FTSYSMHWVR QAPGKGLEWV SGISGSGRST SYADSVKGRF TISRDNSKNT LYLQMNSLRA EDTAVYYCAR DLMAFNLVRA GGFDVWGQGT LVTVSSGGGG SGGGGSGGGG SNWVNVISDL KKIEDLIQSM HIDATLYTES DVHPSCKVTA MKCFLLELQV ISLESGDASI HDTVENLIIL ANDLSSNGN VTESGCKECE ELEEKNIKEF LQSFVHIVQM FINTS |
| 8 | Sushi-Fc fusion | ITCPPPMSVE HADIWVKSYS LYSRERYICN SGFKRKAGTS SLTECVLNKA TNVAHWTTPS LKCIREPKSS DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 9 | Sushi-Fc-anti-CTLA4 scFv fusion | ITCPPPMSVE HADIWVKSYS LYSRERYICN SGFKRKAGTS SLTECVLNKA TNVAHWTTPS LKCIREPKSS DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGKGGG GSGGGGSGGG GSDIQMTQSP SSLSASVGDR VTITCQASQD ISNYLNWYQQ KPGKAPKLLI YDASNLETGV PSRFSGSGSG TDFTFTISSL QPEDIATYYC QQGDAWPWTF GQGTKVEIKG GGGSGGGGSG GGSEVQLVE SGGGLVQPGG SLRLSCAASG FTFTSYSMHW VRQAPGKGLE WVSGISGSGR STSYADSVKG RFTISRDNSK NTLYLQMNSL RAEDTAVYYC ARDLMAFNLV RAGGEDVWGQ GTLVTVSS |
| 10 | Anti-CTLA4 heavy chain | EVQLVESGGG LVQPGGSLRL SCAASGFTFT SYSMHWVRQA PGKGLEWVSG ISGSGRSTSY ADSVKGRFTI SRDNSKNTLY LQMNSLRAED TAVYYCARDL MAFNLVRAGG FDVWGQGTLV TVSSASTKGP SVFPLAPSSK STSGGTAALG CLVKDYFPEP VTVSWNSGAL TSGVHTFPAV LQSSGLYSLS SVVTVPSSSL GTQTYICNVN HKPSNTKVDK KVEPKSCDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW |

TABLE 4-continued

| SEQ ID NO: | Description | Sequence |
|---|---|---|
| | | LNGKEYKCKV SNKALPAPIE KTISKAKGQP REPQVYTLPP SRDELTKNQV SLTCLVKGFY PSDIAVEWES NGQPENNYKT TPPVLDSDGS FFLYSKLTVD KSRWQQGNVF SCSVMHEALH NHYTQKSLSL SPGK |
| 11 | Heavy chain CDR1 | TSYSMH |
| 12 | Heavy chain CDR2 | GISGSGRSTS |
| 13 | Heavy chain CDR3 | RDLMAFNLVR AGGFDV |
| 14 | Light chain CDR1 | QASQDISNYL |
| 15 | Light chain CDR2 | DASNLET |
| 16 | Light chain CDR3 | QGDAWPWT |
| 17 | IL-15 N72D mutant without leader peptide (AA) | NWVNVISDLK KIEDLIQSMH IDATLYTESD VHPSCKVTAM KCFLLELQVI SLESGDASIH DTVENLIILA NDSLSSNGNV TESGCKECEE LEEKNIKEFL QSFVHIVQMF INTS |
| 18 | IL-15 N72D mutant without leader peptide (DNA) | aactgggtga atgtaataag tgatttgaaa aaaattgaag atcttattca atctatgcat attgatgcta ctttatatac ggaaagtgat gttcacccca gttgcaaagt aacagcaatg aagtgctttc tcttggagtt acaagttatt tcacttgagt ccggagatgc aagtattcat gatacagtag aaaatctgat catcctagca aacgacagtt tgtcttctaa tgggaatgta acagaatctg gatgcaaaga atgtgaggaa ctggaggaaa aaaatattaa agaatttttg cagagttttg tacatattgt ccaaatgttc atcaacactt cttaa |

What is claimed:

1. A soluble fusion protein complex comprising:
   (a): a first domain comprising an interleukin-15 (IL-15) peptide wherein the IL-15 peptide comprises SEQ ID NO: 17 or SEQ ID NO: 1;
   (b) a second domain comprising a fusion polypeptide comprising an IL-15 receptor alpha Sushi (IL15RαSu) peptide and an αCTLA4 antibody heavy chain, wherein the αCTLA4 antibody heavy chain has the amino acid sequence of SEQ ID NO: 10; and
   (c) a third domain comprising an αCTLA4 antibody light chain having the amino acid sequence of SEQ ID NO: 3;
   wherein the IL-15 peptide of the first domain binds to the IL-15RαSu peptide of the second domain to form a soluble fusion protein complex.

2. The soluble fusion protein complex according to claim 1, wherein the IL-15 peptide comprises SEQ ID NO: 17.

3. The soluble fusion protein complex according to claim 1, wherein the IL-15 peptide comprises SEQ ID NO: 1.

4. The soluble fusion protein complex according to claim 1, wherein the fusion polypeptide further comprises a peptide linker between an amino terminus of the IL15RαSu peptide and a carboxy terminus of the αCTLA4 antibody heavy chain.

5. The soluble fusion protein complex according to claim 1, wherein the fusion polypeptide comprises SEQ ID NO: 5.

6. The soluble fusion protein complex according to claim 1, wherein the fusion polypeptide further comprises a peptide linker between a carboxy terminus of the IL15RαSu peptide and an amino terminus of the αCTLA4 antibody heavy chain.

7. The soluble fusion protein complex according to claim 6, wherein the fusion polypeptide comprises SEQ ID NO: 4.

8. A pharmaceutical composition comprising the soluble fusion protein complex according to claim 1 and a pharmaceutically acceptable carrier.

9. The pharmaceutical composition according to claim 8, wherein the pharmaceutical composition is formulated for parenteral injection.

10. The pharmaceutical composition according to claim 9, wherein the pharmaceutical composition is formulated for subcutaneous, intravenous, intramuscular, intravesicular, intratumoral or intraperitoneal injection.

11. The pharmaceutical composition according to claim 10, wherein the composition is formulated for intravenous injection.

12. A method of treating melanoma in a subject in need thereof, the method comprising administering to the subject the soluble fusion protein complex according to claim 1.

* * * * *